US008182445B2

(12) United States Patent (10) Patent No.: US 8,182,445 B2
Moubayed et al. (45) Date of Patent: May 22, 2012

(54) METHOD AND SYSTEM FOR CONTROLLED INFUSION OF THERAPEUTIC SUBSTANCES

(75) Inventors: Ahmad-Maher Moubayed, Mission Viejo, CA (US); Oscar E. Hyman, Poulsbo, WA (US); David N. White, San Juan Capistrano, CA (US); Larry L. Wilson, Poway, CA (US); John W. Stevenson, Carlsbad, CA (US); Jay G. Moubayed, Aliso Viejo, CA (US); Linda Thomas, Laguna Niguel, CA (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 152 days.

(21) Appl. No.: 11/731,332

(22) Filed: Mar. 29, 2007

(65) Prior Publication Data

US 2008/0071217 A1 Mar. 20, 2008

Related U.S. Application Data

(63) Continuation of application No. 11/523,794, filed on Sep. 18, 2006.

(51) Int. Cl.
*A61M 31/00* (2006.01)
(52) U.S. Cl. ............ 604/67; 604/65; 604/118; 604/151; 604/153; 604/500; 707/999.107
(58) Field of Classification Search .................... 604/65, 604/67, 118, 151, 153; 705/104.1
See application file for complete search history.

(56) References Cited

U.S. PATENT DOCUMENTS

| | | | |
|---|---|---|---|
| 4,511,353 A * | 4/1985 | Theeuwes ...................... 604/85 |
| 4,670,007 A | 6/1987 | Wheeldon | |
| 4,718,576 A | 1/1988 | Tamura et al. | |
| 4,741,732 A * | 5/1988 | Crankshaw et al. .......... 604/503 |
| 4,756,706 A | 7/1988 | Kerns et al. | |
| 4,785,799 A * | 11/1988 | Schoon et al. ............... 604/500 |
| 4,856,339 A | 8/1989 | Williams | |
| 4,976,151 A | 12/1990 | Morshita | |
| 4,978,335 A | 12/1990 | Arthur | |
| 5,088,981 A * | 2/1992 | Howson et al. ................. 604/31 |
| 5,125,894 A * | 6/1992 | Phipps et al. ................... 604/20 |
| 5,153,827 A | 10/1992 | Coutre et al. | |
| 5,181,910 A | 1/1993 | Scanlon | |
| 5,256,157 A | 10/1993 | Samiotes | |
| 5,389,071 A * | 2/1995 | Kawahara et al. ............ 604/500 |
| 5,401,238 A | 3/1995 | Pirazzoli | |
| 5,474,552 A | 12/1995 | Palti | |

(Continued)

FOREIGN PATENT DOCUMENTS

WO 9636389 11/1996

(Continued)

OTHER PUBLICATIONS

Office Action dated Feb. 23, 2009 for U.S. Appl. No. 11/523,794.

(Continued)

*Primary Examiner* — Nicholas Lucchesi
*Assistant Examiner* — Scott Medway
(74) *Attorney, Agent, or Firm* — K&L Gates LLP

(57) ABSTRACT

Programmable infusion systems and method for controlled infusion of diagnostic or therapeutic substances (e.g., drugs, biologics, fluids, cell preparations, etc.) into the bodies of human or animal subjects.

15 Claims, 8 Drawing Sheets

U.S. PATENT DOCUMENTS

| | | | | |
|---|---|---|---|---|
| 5,620,312 | A | * | 4/1997 | Hyman et al. ............... 417/474 |
| 5,683,367 | A | | 11/1997 | Jordan |
| 5,733,259 | A | * | 3/1998 | Valcke et al. ................ 604/66 |
| 5,756,327 | A | | 5/1998 | Sasanfar |
| 5,782,805 | A | | 7/1998 | Meinzer et al. |
| 5,791,881 | A | | 8/1998 | Moubayed |
| 5,901,246 | A | | 5/1999 | Hoffberg et al. |
| 5,924,852 | A | | 7/1999 | Moubayed |
| 5,938,636 | A | | 8/1999 | Kramer et al. |
| 5,978,702 | A | | 11/1999 | Ward et al. |
| 6,164,921 | A | | 12/2000 | Moubayed |
| 6,269,340 | B1 | | 7/2001 | Ford et al. |
| 6,371,732 | B1 | | 4/2002 | Moubayed |
| 6,421,650 | B1 | * | 7/2002 | Goetz et al. ................. 705/3 |
| 6,562,001 | B2 | | 5/2003 | Lebel et al. |
| 6,659,980 | B2 | | 12/2003 | Moberg |
| 6,696,924 | B1 | * | 2/2004 | Socinski ..................... 700/213 |
| 6,740,075 | B2 | * | 5/2004 | Lebel et al. ................. 604/891.1 |
| 6,749,586 | B2 | | 6/2004 | Vasko |
| 6,854,620 | B2 | | 2/2005 | Ramey |
| 7,060,059 | B2 | * | 6/2006 | Keith et al. ................. 604/504 |
| 7,061,831 | B2 | | 6/2006 | De La Huerga |
| 7,506,807 | B2 | * | 3/2009 | Durrell et al. ............... 235/382 |
| 7,716,071 | B2 | * | 5/2010 | Gold .............................. 705/3 |
| 2001/0031944 | A1 | | 10/2001 | Peterson et al. ............. 604/65 |
| 2002/0077852 | A1 | | 6/2002 | Ford et al. |
| 2002/0090388 | A1 | * | 7/2002 | Humes et al. ............... 424/422 |
| 2002/0107476 | A1 | | 8/2002 | Mann et al. |
| 2002/0188465 | A1 | | 12/2002 | Gogolak et al. |
| 2002/0198473 | A1 | * | 12/2002 | Kumar et al. ................ 600/595 |
| 2003/0073609 | A1 | * | 4/2003 | Pinkerton .................... 514/1 |
| 2003/0078534 | A1 | | 4/2003 | Hochman et al. |
| 2003/0114836 | A1 | * | 6/2003 | Estes et al. ................. 604/890.1 |
| 2004/0019607 | A1 | | 1/2004 | Moubayed |
| 2004/0073177 | A1 | | 4/2004 | Hickle |
| 2004/0172283 | A1 | | 9/2004 | Vanderveen |
| 2004/0193025 | A1 | * | 9/2004 | Steil et al. .................. 600/316 |
| 2004/0193378 | A1 | * | 9/2004 | Gut et al. .................... 702/20 |
| 2005/0277890 | A1 | | 12/2005 | Stewart et al. |
| 2006/0047538 | A1 | | 3/2006 | Condurso et al. |
| 2006/0155589 | A1 | * | 7/2006 | Lane et al. .................. 705/4 |
| 2006/0229557 | A1 | | 10/2006 | Fathallah et al. |
| 2008/0162352 | A1 | * | 7/2008 | Gizewski .................... 705/50 |

FOREIGN PATENT DOCUMENTS

| | | |
|---|---|---|
| WO | 0047255 | 8/2000 |
| WO | 03063932 | 8/2003 |
| WO | 2005118054 | 12/2005 |

OTHER PUBLICATIONS

Office Action dated Apr. 6, 2009 for U.S. Appl. No. 11/731,585.
Office Action dated Jun. 2, 2009 for U.S. Appl. No. 11/731,274.
Office Action dated Nov. 19, 2009 for U.S. Appl. No. 11/731,274.
Office Action dated Nov. 25, 2009 for U.S. Appl. No. 11/731,342.
Office Action dated Dec. 11, 2009 for U.S. Appl. No. 11/523,794.
Office Action dated Feb. 5, 2010 for U.S. Appl. No. 11/731,585.
Office Action dated Mar. 4, 2010 for U.S. Appl. No. 11/731,274.
Office Action dated Apr. 21, 2010 for U.S. Appl. No. 11/523,794.
Final Office Action for U.S. Appl. No. 11/731,342 mailed Jun. 25, 2010.
Non-Final Office Action for U.S. Appl. No. 11/731,342 mailed Nov. 29, 2010.
Final Office Action for U.S. Appl. No. 11/731,342 mailed May 11, 2011.
Non-Final Office Action for U.S. Appl. No. 11/731,585 mailed Aug. 5, 2010.
Final Office Action for U.S. Appl. No. 11/731,585 mailed Jan. 21, 2011.

* cited by examiner

METHOD AND SYSTEM FOR CONTROLLED INFUSION OF THERAPEUTIC SUBSTANCES

RELATED APPLICATION

This is a continuation of U.S. patent application Ser. No. 11/523,794 filed Sep. 18, 2006, the entire disclosure of which is expressly incorporated herein by reference.

FIELD OF THE INVENTION

The present invention relates generally to medical devices and methods and more particularly to programmable infusion pump systems and their uses in the treatment of medical disorders.

BACKGROUND OF THE INVENTION

Various types of programmable infusion pumps have been used to deliver controlled infusions (e.g., intravenous infusions, epidural infusions, subcutaneous infusions, enteral infusions, etc.) to patients in hospital and out-of-hospital settings. Programmable infusion pumps are used to administer a wide range of drugs, biological therapies and other substances, including but not limited to cancer chemotherapy, analgesic medications, Immune Globulin therapy, insulin, etc. Programmable infusion pumps typically include safety features that control or limit the rate of infusion and the amount of solution delivered to the patient, thereby preventing inadvertent overdosing, underdosing and/or infusion rate-related side effects. Some programmable infusion pumps also include other safety features such as automated air-in-line detectors, etc. These types of safety features are not typically available with non-programmable pumps or hanging intravenous drips.

The infusion pump systems of the prior art have included varying degrees of programmability and/or automation. Examples of infusion pump systems that are programmable and/or have some degree of automation include, but are not limited to, those described in U.S. Pat. Nos. 4,670,007 (Wheeldon et al.); 4,978,335 (Arthur, III); 4,976,151 (Morshita); 4,856,339 (Williams); 5,256,157 (Samiotes, et al.); 5,756,327 (Sasanfar, et al.); 5,683,367 (Jordan, et al.); 6,269,340 (Ford, et al.); 6,854,620 (Ramey) and 6,659,980 (Moberg, et al.) as well as United States Patent Application Publication Nos. 2004/0019607 (Moubayed et al.) and 2004/0172283 (Vanderveen et al.).

One particular use for programmable infusion pump technology is in the administration of Immune Globulin (Ig) therapy. Immune Globulin may be infused intravenously (e.g., Intravenous Immune Globulin (IVIG) Therapy) or subcutaneously (e.g. Subcutaneous Immune Globulin (SQIG) therapy). Immune Globulin therapies have been used to treat primary immunodeficiencies (e.g., congenital agammaglobulinemia, hypogammaglobulinemia, common variable immunodeficiency, X-linked immunodeficiency with hyperimmunoglobulin M, severe combined immunodeficiency (SCID) and Wiskott-Aldrich syndrome). Also, IVIG therapy may be used in the treatment of Kawasaki Syndrome, B-Cell Chronic Lymphocytic Leukemia, Idiopathic Thrombocytopenic purpura (ITP), acute graft-versus-host disease associated interstitial pneumonia (infectious or idiopathic) after bone marrow transplantation (BMT), human immunodeficiency virus (HIV), as a treatment for Acute Guillain-Barré Syndrome, refractory dermatomyositis, hyperimmunoglobulinemia E syndrome, Lambert-Eaton Myasthenic Syndrome, Relapsing-Remitting Multiple Sclerosis, Parvovirus B19 Infection and associated anemia, Chronic Inflammatory Demyelinating Polyneuropathies, Multifocal Motor Neuropathy (MMN), infectious diseases, adrenoleukodystrophy, acquired Factor VII inhibitors, acute lymphoblastic leukemia, anemia, autoimmune hemolytic anemia, aplastic anemia, diamond Blackfan anemia, Aplasia, Pure Red Cell anemia, asthma, inflammatory chest disease, Behcet's syndrome, chronic fatigue syndrome, clostridium difficile toxin, congenital heart block, cystic fibrosis, intractable pediatric epilepsy, juvenile arthritis, myositis, polymyositis, multiple myeloma and immunoproliferative neoplasms, motor neuron syndromes, myasthenia gravis, myelopathy associated with Human T-cell leukemia/lymphoma virus-I, nephrotic syndrome, membraneous neuropathy, paraproteinemic neuropathy, euthyroid opthalmopathy, recurrent otitis media, pemphigus vulgaris, pemphigus foliaceus, paraneoplastic pemphigus, progressive lumbosacral plexopathy, post-transfusion purpura, recurrent fetal loss, renal failure, rheumatoid arthritis, systemic lupus erythematosus and related cytopenia, nephritis, CNS involvement, vasculitis, pericarditis, or pleural effusion, thrombotic thrombocytopenic purpura, nonimmune thrombocytopenia, neonatal alloimmune thrombocytopenia (pre- and postnatal), septic thrombocytopenia, quinine induced thrombocytopenia, transfusion reactions, uveitis, systemic vasculitic syndromes, acquired Von Willebrand's syndrome and others.

Immune Globulin infusions must be carefully prescribed and administered. IVIG infusions are often administered by an infusion protocol whereby the rate of infusion is increased in a step-wise fashion. Prior to each increase in the infusion rate (e.g., each "step up"), the patient is monitored for signs of adverse reaction. If no adverse reaction is noted and the patient appears to be tolerating the infusion, then the infusion rate is increased (e.g., stepped up). The types of adverse reaction that may occur as a result of IVIG infusion include migraine headache, flushing, nausea, vomiting, chills and others. There is also a risk of more serious, sometimes life-threatening reactions, for example, risk of thrombus formation. Particular care must be given to patients having certain health issues such as a history of stroke, heart attack, blood vessel disease, IgA or IgG deficiencies or blood clots.

With the heightened emphasis on cost-effectiveness and cost-containment in health care, home infusion therapy is becoming increasingly commonplace. Home infusion therapy generally involves the administration of medications, for example, Immune Globulin infusions using intravenous, or subcutaneous routes, in the patient's home rather than in a physician's office or hospital. Infusion therapies in the home are typically administered by a home health care worker having some training in the operation of infusion equipment and the administration of biologic therapies, but in some cases may be administered by a patient himself. Thus, it can be appreciated that there is a need for systems and methods that incorporate careful monitoring of patient reactions and vital signs during administration of infusion therapies, for example, IVIG.

Other particular uses for programmable infusion pumps include, but are not limited to, the administration of analgesics, anesthetics, cancer chemotherapy, antibiotics, gene therapy agents, anti-venoms and other drugs or substances that require carefully controlled and/or monitored infusion to avoid harmful reactions, overdosing, allergic responses, anaphylactic responses, other idiosyncratic responses, etc.

There remains a need in the art for the development of new programmable infusion systems that provide for improved infusion control and symptom/side effect monitoring during and/or after the infusion.

SUMMARY OF THE INVENTION

In accordance with the present invention there is provided a system for administering a substance to a human or non-human animal subject. In general, this system comprises a) a pump, b) a substance administration conduit for delivering the substance to the subject's body, c) a subject database containing information on at least one human or non-human animal subject and d) a controller that is in communication with the pump and issues control signals to the pump, such controller being adapted to access information on the subject from the subject information database. The subject database may contain various types of information that is specific to each human or animal subject, including for example; name, address, age, body weight, medical history, a list of other medications received, allergies, reaction(s) to previous infusions, preferred vascular access site(s), prescriptions for substances to be infused, etc. In some embodiments, the subject database may include information obtained from personal responses provided by the subject regarding his/her reaction to the current or prior infusions of the substance. In such embodiments, the system may include apparatus for posing queries to the subject and for receiving/storing the subject's responses to such queries. Alternatively or additionally, in some embodiments, the subject database may include information obtained by monitoring the subject's bodily or physiologic responses to the current or prior infusions of the substance. In such embodiments, the system may include apparatus (e.g., a feedback loop) for monitoring bodily or physiologic variable(s) that are potentially indicative of the subject's bodily and or physiologic responses to an infusion (e.g., heart rate, blood pressure, body temperature, respiratory rate, oxygen saturation, galvanic skin response, airway resistance, etc.) and for receiving/storing information relating to changes in those monitored variables.

Further in accordance with the invention, the above-summarized system may optionally include a substance database that contains information on at least one substance that the system may administer to subject(s). In embodiments that include the substance database, the controller may be further adapted to access substance information from the substance database. The substance database may contain one or more pre-defined, substance-specific infusion protocols that may be used for administration of a particular substance and/or other types of information on specific therapeutic substances (e.g., dosage information, recommended infusion rate information, substance-substance interactions, known side effects or adverse reactions, etc.) on various substance(s) (e.g., drugs, biologics, etc.). In some embodiments, the substance database may group substance information by category (e.g., therapeutic categories, drug categories, etc.). Optionally, the system may incorporate a user interface (e.g., a keyboard, touch screen, voice recognition or other data input apparatus) or may have a hard wired or wireless connection to a separate data input apparatus or data storage device (e.g., a wired or wireless network, a personal computer, personal digital assistant, laptop computer, disc drive, USB flash drive, etc.) whereby substance-specific infusion protocols or other substance information may be transferred (e.g., loaded) to and stored by the substance database. In this regard, a user may create one or more prescribed infusion protocols for a particular substance and may then manually input or download those custom made, substance-specific infusion protocols to be stored in the substance database in connection with the particular substance to which they pertain.

Still further in accordance with the invention, the above-summarized system may optionally include an infusion database containing infusion information (e.g., generic or pre-defined infusion parameters or protocols that are not specific to a particular substance) and the controller may be further adapted to access infusion parameter information from the infusion database. The infusion database may contain various types of infusion information including, for example, a variety of pre-set infusion protocols, specific infusion parameters (e.g., rate(s), volume(s) and time(s). The term "infusion protocol" as used herein refers to a series of pump control instructions that control some or all of the following: rate(s) at which the pump will infuse the substance, when change(s) in infusion rate will occur, the volume of infusate to be infused, the duration of infusion, the infusion profile, the infusion schedule, etc. In some cases the infusion protocol may be a step-wise protocol wherein the substance is infused at a first rate for a first infusion period (e.g., a period of time or until a predetermined amount of the substance has been delivered) then to change to a second flow rate for a second infusion period. This may repeat for one or more subsequent infusion periods (e.g., the total number (n) of infusion periods may be 2 or more). In other cases the infusion protocol may provide for continual increase and/or decrease of the infusion rate (e.g., a continuous ramp up and/or down) rather than changing infusion rates at discrete periods as in the step-wise protocol.

These and other aspects and advantages of the present invention are apparent in the following detailed description and claims, particularly when considered in conjunction with the following drawings in which like parts are identified by like reference numerals.

DETAILED DESCRIPTION OF THE INVENTION

The following detailed description and the accompanying drawings are intended to describe some, but not necessarily all, examples or embodiments of the invention. The contents of this detailed description and the accompanying drawings are not necessarily all-inclusive and do not limit the scope of the invention in any way.

Figure 1:
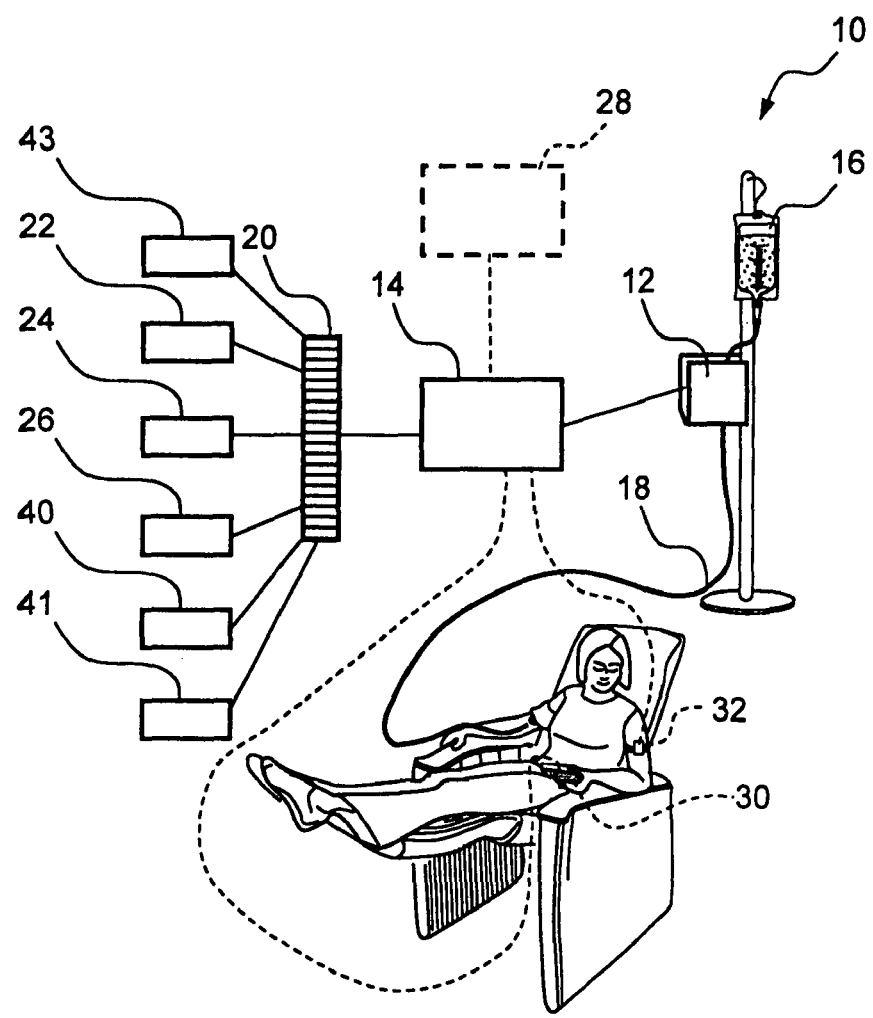
FIG. 1 is a general diagram of an infusion system of the present invention.

FIG. 1 shows the programmable infusion system 10 of the present invention. In this example, the system 10 generally comprises an infusion pump 12, an infusate-containing vessel 16, an infusion conduit 18, a controller 14 for controlling the pump, a data storage medium 20 accessible by the controller 14. The data storage medium 20 is useable for storage of, and access to, one or more databases such as a substance protocol database 22 and/or a subject protocol database 24 and/or and infusion protocol database 26 and/or a substance reference library 40 and/or system configuration parameters 41 and/or a history file 43. In embodiments that include a substance reference library 40, such substance reference library 40 may be a separate database or may be incorporated as part of the substance protocol database 22.

In addition, system 10 may include one or more interfacing device(s) 28 (e.g., a personal computer 28a, USB flash memory drive 28a', personal digital assistant (PDA) 28b, barcode reader 28c, and/or telephony modem) accessible to controller 14. Further, a user interface device 30 (e.g., touch screen, mouse, keyboard, voice recognition system, or other data input apparatus) may be connected to the controller 14 and may be used to control and program the system.

The components of the system, such as the controller 14, interface devices 28, data storage medium 20 and user interface device 30, may be incorporated as subsystems within pump 12, or may exist as separate subsystem(s) external to the pump 12 or may be integrated along with the pump 12 in a common housing, console, cart, etc. Alternative embodiments include all possible combinations wherein one or more subsystem(s) is/are incorporated within the pump 12 or may be integrated along with the pump 12 in a common housing, console, cart, etc while one or more other subsystem(s) are external to the pump 12. For example, controller 14 and data storage medium 20 could be incorporated into the pump 12 or may be integrated along with the pump 12 in a common housing, console, cart, etc while user interface device 30 and interface devices 28 could be external to the pump 12 or the housing, console, cart of other body or enclosure in which the pump is located.

It will be appreciated that the pump 12 may be any suitable type of pump. In some embodiments a peristaltic pump may be employed. Such peristaltic pump may comprise any suitable type of peristaltic pump, including but not limited to traditional peristaltic pumps, curvilinear peristaltic pumps such as those described in U.S. Pat. Nos. 6,371,732, 6,164,921 and/or 5,791,881, a linear peristaltic pump as described in U.S. Pat. No. 5,924,852 or a rotary axial peristaltic pump such as that described in copending U.S. patent application Ser. No. 11/212,931, the entire disclosures of such patents and patent application being expressly incorporated herein by reference. Basically, a "rotary axial peristaltic pump" comprises a platen having a platen surface, a tube positioned adjacent to the platen surface, a cam that rotates about a rotational axis, such cam having a cam surface that is spaced apart from the platen surface and a plurality of fingers, each finger having a longitudinal axis that is substantially parallel to the rotational axis of the cam. The fingers engage the cam surface such that, as the cam rotates about the rotational axis, the fingers will move axially back and forth, sequentially compressing the tube against the platen surface, thereby causing peristaltic movement of fluid through the tube.

Figure 3:
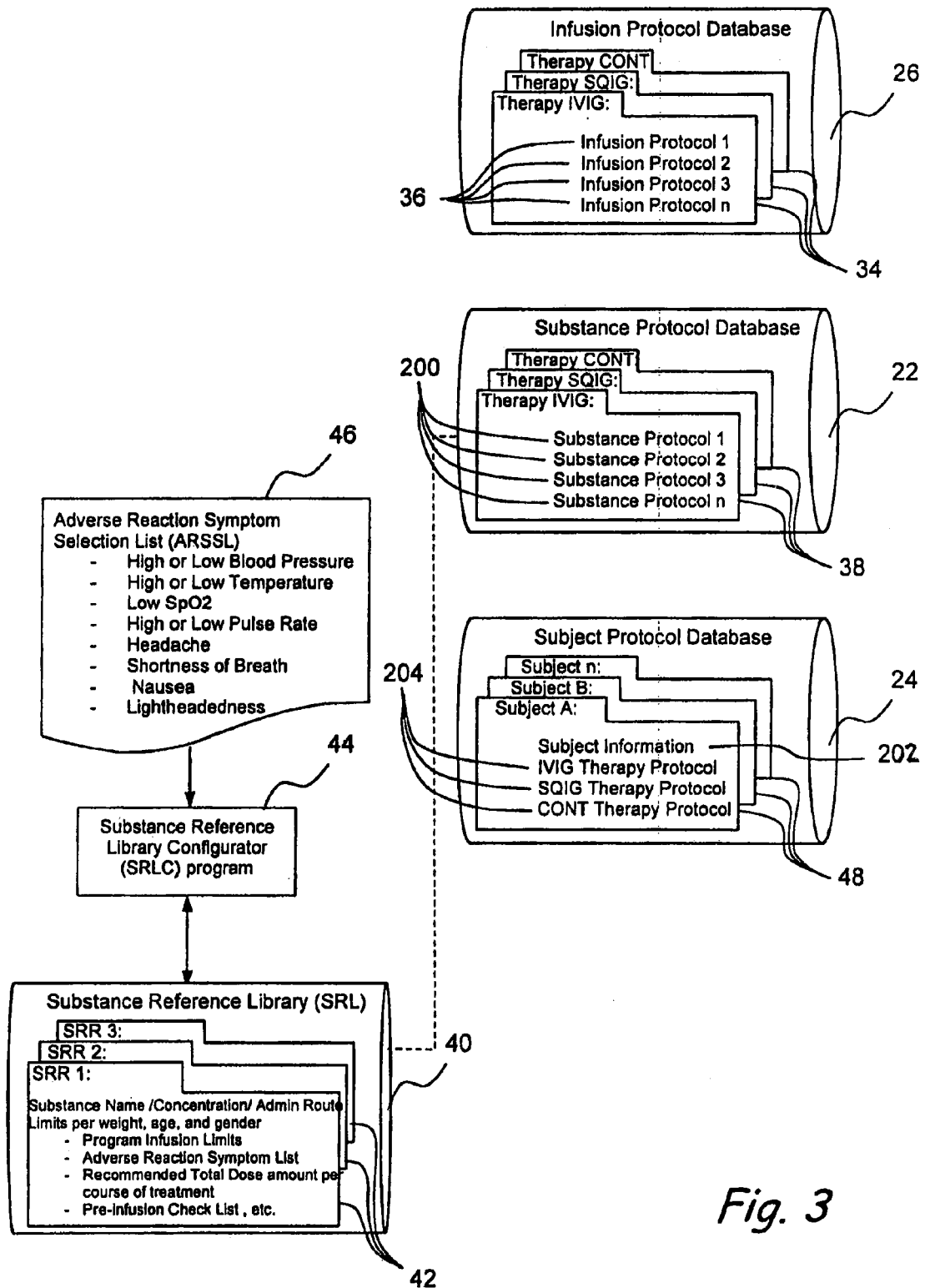
FIG. 3 is a diagram of various databases and records that may be incorporated into or accessed by an infusion system of the present invention.

The system 10 may be in communication (via wired or wireless connection) with one or more external interface devices 28. Controller 14 may be programmed to transfer all or part of any database (e.g., all or part of the substance protocol database 22, subject protocol database 24, therapy-type protocol database 26, substance reference library database 40, system configuration database 41 and/or history database 43 to or from external interface device(s) 28. For example, as illustrated in FIG. 3, the user may create one or more substance protocols 200, subject protocols 204, or therapy-type infusion protocols 36 on external interface devices 28 and subsequently command the system 10, via the user interface device 30, to copy, or download, the protocols to their respective databases on in the data storage medium 20. Likewise, the history file 43 may be copied, or uploaded, from the data storage medium device 20 to external interface devices 28 as commanded by the user In one embodiment, after a new substance protocol has been downloaded or created on the system 10 and if a substance reference record 42 exists in the substance reference library 40 for the substance incorporated in the new substance protocol, the program operating in the controller 14 may check each parameter of the new substance protocol against parameter limits found in the substance reference record 42 and against the system configuration parameters 41. If any parameter of the new substance protocol violates the limits of the substance reference record 42 or the system configuration parameters 41, the controller 14 may then provide an error signal and/or disallow storage of the new substance protocol to the substance protocol database 22 and prevent execution of the new substance protocol. In some embodiments, the program operating in the controller may allow the violation to be overridden such that a new substance protocol, with an out-of-limit parameter, may be stored and/or executed. Permission to override a limit violation may be controlled by proper authorization techniques (e.g., by entry of a supervising physician's code or PIN).

In embodiments that incorporate a subject protocol database 24, subject protocol records may contain subject information 202 containing various information that is specific to a human or animal subject, including for example the subject's name, address, age, body weight, gender, medical history, a list of other medications received, allergies, reaction(s) to previous infusions, preferred vascular access site(s), prescriptions for substance to be infused, etc. Subject information 202 may be input into the subject protocol database 24 through the user interface 30 or downloaded from another source such as interface devices 28 (e.g., personal computer 28a, USB flash drive device 28a', PDA 28b, barcode reader 28c where a barcode containing such information is read, or connected modem 28d, etc.)

In one embodiment, a barcode label attached to the infusate vessel 16 contains information regarding the make up and/or substance of the infusate contained in the vessel 16, and/or information about the subject to receive the administration of the infusate, and/or the definition of the infusion protocol for the administration of the infusate. By use of a barcode reader 28c, the barcode label may be read and its information transferred to controller 14 where the program running on the controller 14 may validate the barcode label information against a substance reference record 42, if a correlating substance reference record exists in the substance reference library 40, and against the system configuration parameters 41. If the infusion protocol parameters within barcode label information violate one or many parameter limits found in an available substance reference record 42 or the system configuration parameters 41, the controller 14 may prevent the barcode information from being stored or executed; however, such violation may be overridden with proper authorization.

Further, barcode subject data that is inconsistent with any available subject information 48 found in the subject protocol database 24 may prohibit the storage or execution of the infusion protocol; however, such prohibition may be overridden when properly authorized.

In embodiments of the system 10 that incorporate the optional subject query/response device 30 (also known as the user interface device) such query/response device 30 may be used to pose queries to the subject at certain times (e.g., specific times before, during or after a dose of the infusion) and to input to the controller 14 the subject's responses to those queries.

For example, the subject query/response device 30 may comprise a terminal that has a monitor or screen on which specific questions are displayed in written form and/or a speaker that poses audible queries to the subject in spoken form. Further, the input apparatus of the subject query/response device 30 may comprise a touch screen, mouse, keypad, switch(es), joystick, encoder wheel, or other apparatus by which the subject may input their response to presented queries. The controller 14 may be in communication with the query/response device 30 and programmed to present the queries to the subject at the desired points in time and to receive the subject's responses to the queries and to evaluate and store the responses. As part of the evaluation process, the controller 14 may be programmed to compare the subject's query responses to a reference library containing acceptable and/or unacceptable responses. If the subject's response to a query is determined to be unacceptable, the controller 14 may be programmed to provide an alarm or notice to the user and/or halt the infusion and/or alter the infusion's execution (e.g., reduce the infusion rate or stop the infusion.) For example, during the administration of an infusion of a Drug X, the controller may query the subject at different points in time as to whether the subject is experiencing adverse reaction symptoms that are known to occur in some individuals who receive Drug X (e.g., the query might be: Are you currently experiencing hives or itchy skin?, Are you currently experiencing wheezing or shortness of breath?, Are you currently experiencing blurred vision?, etc.) The subject then answers each query using the input apparatus of the subject query/response device 30. The controller 14 then compares the subject's query responses to a reference database of acceptable and/or unacceptable responses and determines if the subject's query responses are indicative of an adverse reaction. If the subject's query responses are determined to be indicative of an adverse reaction, the controller 14 may then effect remedial measure(s) in accordance with its programming. For example, if a subject's response indicates that he or she has begun to suffer a headache, the controller 14 may respond by changing the control signals to the pump 12 to reduce the infusion rate by a predetermined amount (e.g., 50%) and may then re-query the subject at some later time, or at periodic time intervals (e.g., 5 minutes) to determine if the headache is continuing. If the subject's query response indicates that he or she is no longer experiencing the headache, the controller 14 may then signal the pump 12 to continue the infusion in accordance with the originally selected protocol or some reduced rate protocol in accordance with the controller's programming. On the other hand, if upon re-query the subject responds that he or she is continuing to experience the headache, the controller 14 my signal the pump to further reduce the rate of infusion or to halt the infusion and/or alert the operator in accordance with the manner the controller is programmed.

Alternatively or additionally, in some embodiments, the system may incorporate sensor(s) 32 (e.g., vital sign monitors) for sensing certain bodily or physiologic variables and communicating those sensed variable (or indications of changes in sensed variables) to the controller 14. The bodily or physiologic variables monitored by the sensor(s) 32 may include bodily and/or physiologic variable that change when a subject is experiencing an adverse reaction to an infusion (e.g., heart rate, blood pressure, body temperature, respiratory rate, oxygen saturation, carbon monoxide saturation, galvanic skin response, airway restriction, etc.) The controller 14 may be programmed to issue special or modified control signals to the pump 12 (e.g., to slow the infusion rate or halt the infusion) and/or to issue an alarm signal to the operator in the event that the controller 14 receives a signal from a sensor 32 indicative of an adverse reaction or other untoward effect of the infusion. Also in embodiments of the system 10 that incorporate the optional subject query/response device 30 as well as the optional sensor(s) 32, the controller 14 may be programmed to pose specific queries to the subject in order to confirm possible indications of adverse reactions detected by the sensor(s) 32. Consider for example, hypothetical Drug Z, which when infused too rapidly is known to cause an adverse reaction characterized by an increase in heart rate and nausea. In a case where Drug Z is being infused too rapidly for the subject, the sensor(s) may communicate to the controller the subject's heart rate in a continuous fashion. The controller can then detect an increase of heart rate and cause the subject query/response device 30 to ask the subject whether he or she is experiencing nausea. If the subject responds in the negative, the controller 14 may allow the pump 12 to continue the infusion in accordance with the original infusion protocol while continuing to monitor for further changes in heart rate and/or periodically querying the subject for the occurrence of nausea. On the other hand, if the subject responds that he or she is experiencing nausea, the controller 14 may signal the pump 12 to modify the infusion protocol (e.g., decrease the rate of infusion and/or forego further increases in the rate of infusion) or to halt the infusion and/or to provide an alarm to the operator, in accordance with the manner in which the controller is programmed.

In embodiments of the system 10 that incorporate an infusion protocol database 26, such infusion protocol database 26 may contain pre-defined, non-specific infusion protocols or preset infusion parameters which the user may select for use without regard to the substance to be infused or the subject to receive the infusion. When a non-specific infusion protocol has been selected from the infusion protocol database 26, or programmed via the user interface device 30, the controller 14 may check the parameters of the non-specific infusion protocol against the limits contained in the system configuration parameters 41 by the controller 14 to determine that all parameters are within operating limits. If any parameter of the non-specific infusion protocol violates the system configuration parameters 41, the controller 14 may then provide an error signal and disallow execution of the non-specific infusion protocol; however, such violation may be overridden with proper authorization.

Further, in embodiments that include a substance reference library 40, the operator may, by use of the user interface device 30, choose to associate the non-specific infusion protocol to a particular substance reference record 42 found in the substance reference library 40. Once the association has been made, the controller 14 may check the parameters of the non-specific infusion protocol against the limits found in the substance reference record 42. If the parameters of the non-specific infusion protocol violate the parameters of the substance reference record 42, the controller 14 may then provide an error signal and prevent execution of the non-specific infusion protocol; however, such violation may be overridden with proper authorization. Further, with proper authorization, the operator may modify the non-specific infusion protocol so that none of its parameters are in violation of the selected substance reference record 42.

Lastly, in embodiments that include a subject protocol database 24, the operator may, by use of the user interface device 30, choose to associate the non-specific infusion protocol to a particular subject protocol record 48 found in the subject protocol database 24. Once the association has been made, the controller 14 may store the non-specific infusion protocol as a subject protocol record 48 in the subject protocol database 24. In addition, if the non-specific infusion protocol had previously been associated with a substance reference record 42, the additional association with a subject protocol record 48, thereby identifying a subject, may cause the parameters of the non-specific infusion protocol to be checked against the substance reference record 42 limits that are subject specific. For example, where a non-specific infusion protocol has been associated with a substance reference record (e.g., Drug X which contains a limitation that the total amount infused shall not exceed 10 mg per 100 lbs of subject weight) and the non-specific infusion protocol is later associated with a subject protocol record (e.g., for Mr. Jones which includes information about Mr. Jones' weight) then the controller 14 may determine if the substance reference record limitation for this specific subject is in violation given the non-specific infusion protocol parameter regarding total amount of substance to be infused. Where the controller determines that a violation exists, the controller 14 may then provide an error signal and prevent execution of the non-specific infusion protocol; however, such violation may be overridden with proper authorization. Further, with proper authorization, the operator may modify the non-specific infusion protocol so that none of its parameters are in violation.

Set forth below is a detailed example of an embodiment of the present invention.

EXAMPLE

Smart Immune Globulin (SIG) Infusion System and Method

Figure 2:
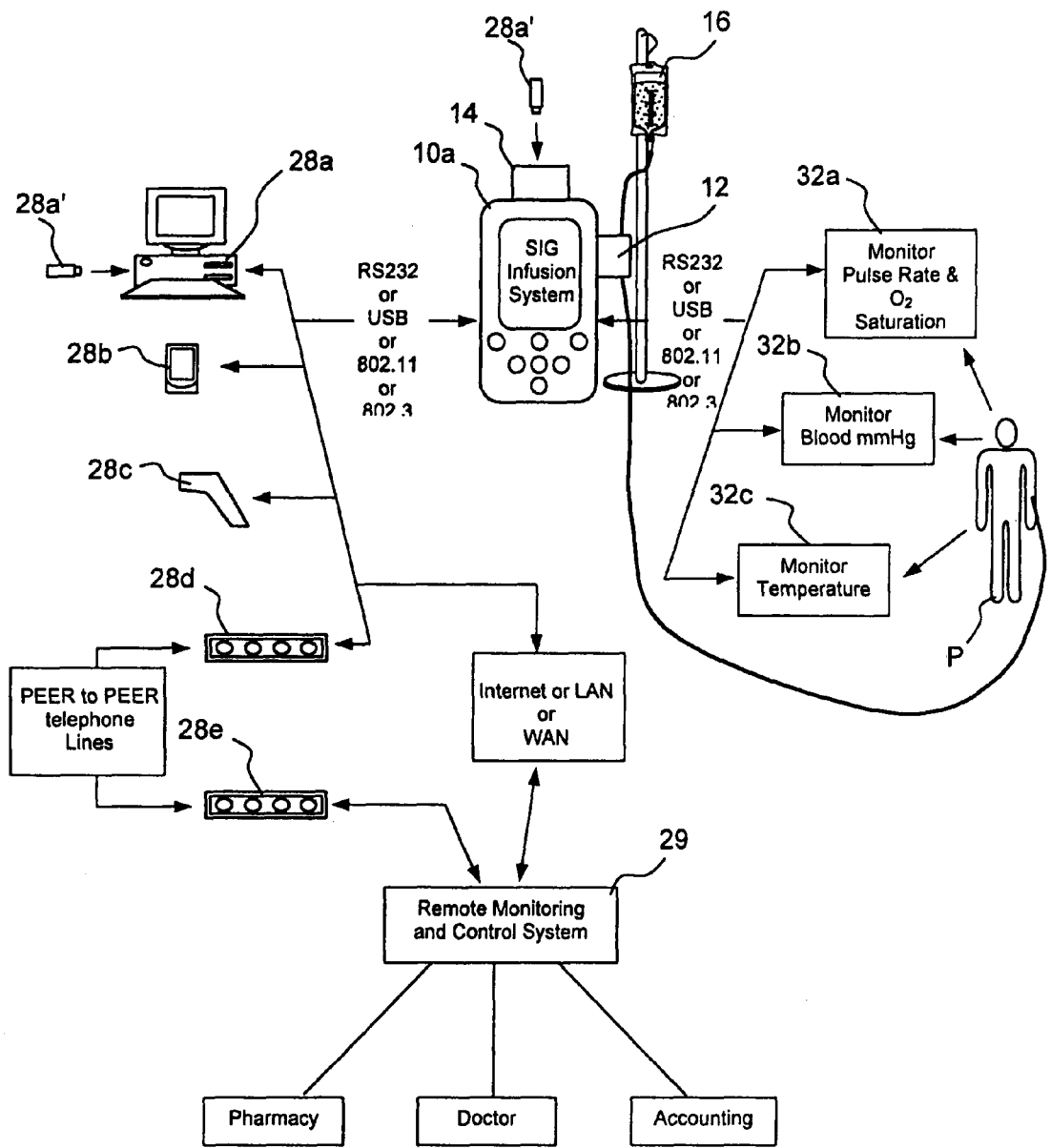
FIG. 2 is a diagram of one embodiment of an infusion system of the present invention useable to administer IVIG therapy and other biologic therapies.

Referring to FIG. 2, the SIG infusion system of this example includes a pump 10a, which pump includes a controller, motor and electronics to operate the pump, user interface device (e.g., liquid crystal display and a touch screen overlaid on the LCD), various operator keys, a sound producing audio subsystem, a microphone subsystem, a compact flash connector into which a IEEE 802.11 (WiFi) wireless interface adaptor or Bluetooth adaptor can be mounted, a Universal Serial Bus (USB) host interface connector, a USB client interface connector, a IEEE 802.3 ethernet connector, and a EIA RS-232 serial interface connector. The pump 10a may include one or more sensor(s) operating on the conduit 18 for detecting occlusions of the conduit 18 and/or air bubbles within the conduit 18 as may occur when the infusate bag or vessel 16 becomes empty, inadvertently disconnected or air leaks into the conduit 18 or vessel 16. The SIG infusion system of this example also incorporates several interface devices which communicate directly with the controller 14. These interface devices include: a personal computer 28a, a removable USB flash driver 28a', a personal digital assistant 28b, a barcode reader 28c, a first telephony modem 28d and a second telephony modem 28e for providing connectivity to various computer networks, personal computers, vital signs monitoring equipment, and other peripheral devices. Personal computer 28a can be connected directly to the controller 14 through interfaces of EIA RS232, USB client, IEEE 802.3 Ethernet, or IEEE 802.11b wireless interface.

Through these interfaces the interface devices (28a, 28a', 28b, 28c, 28d, and 28e) may communicate with the controller 14 for the purpose of sending and retrieving files or records to/from the substance protocol databases 22, the subject protocol database 24, the infusion protocol database 26, and the substance reference library 40 (if stored separately from the substance protocol databases 22). In addition, the personal computer 28a can monitor the activities of the SIG infusion system 10a when connected. Alternatively or additionally, a personal digital assistant (PDA) 28b can be used to communicate with the SIG infusion system via a hard wired connection such as EIA RS232, USB, and/or by a wireless interface such as an IEEE 802.11b wireless interface and perform many of the same functions as the personal computer.

In some embodiments of the invention, the personal computer 28a and the SIG infusion system 10a may both be equipped with ports, such as USB ports, so that a transfer device such as a USB flash drive device 28a' can be used as a medium for the transfer of files or data between the personal computer 28a and the SIG infusion system 10a. For example, an infusion protocol may be created on the personal computer 28a, then copied to the USB flash drive 28a' and, thereafter, the USB flash drive 28a' may be transported to and inserted in the corresponding USB port of the SIG infusion system 10a such that the files or data may be read directly by the controller 14 or transferred to the controller's memory from the USB flash drive 28a' and stored in the infusion protocol database 26.

An optional barcode reader 28c (e.g., DS6608, Symbol Technologies, Holtsville, N.Y. or LG2, Opticon, Inc., Orangeburg, N.Y.) can interface to the SIG infusion system by means of EIA RS232, USB, or IEEE 802.11b wireless interface for the purpose of reading and communicating barcode information from barcode symbols located, for example, on subject's ID bracelet, drug reservoir, and/or operator's ID badge. Further, the barcode reader 28c can be used to program the SIG infusion system by reading a protocol, subject information and/or other data encoded on a barcode symbol affixed to the bag or other vessel 16 containing an Immune Globulin preparation to be infused.

FIG. 2 also shows the connecting of various sensors (also known as vital sign monitors) 32a, 32b, 32c to the controller 14 to monitor certain of the subject's vital signs. In particular, in this example, a first sensor 32a such as a pulse oximeter device (e.g., Radical, Masimo Corporation, Irvine, Calif. or OxiMax® N-595, Nellcor, Pleasanton, Calif.) is used to monitor pulse rate and oxygen saturation, a second sensor 32b such as a blood pressure monitor (e.g., UA-767PC, A&D Co., Ltd., Saitama, Japan or HEM-711AC, Omron Corporation, Kyoto, Japan) is used to monitor blood pressure and a third sensor 32c such as a body temperature monitoring device (e.g., Spot Vital Signs, Welch Allyn, Beaverton, Oreg. or DataTherm, Geratherm Medical AG, Geschwenda, Germany) is used to monitor the subject's body temperature. These sensors 32a, 32b, 32c are in communication with the controller 14 by way of a wired or wireless connections, such as an EIA RS232, USB, or IEEE 802.11b wireless interface. Pulse rate and oxygen saturation sensor 32a provides an automated acquisition means of obtaining subject pulse rate and oxygen saturation level. Blood pressure sensor 32b provides an automated means of obtaining the current diastolic and systolic blood pressure of the subject. Temperature sensor 32c provides an automated means of obtaining the subject's temperature. These vital signs sensors 32a, 32b, 32c provide feedback to the SIG infusion system 10a during the infusion procedure and the controller 14 is programmed to analyze such feedback for signs indicating that the subject is having (or is about to have) an adverse reaction to the infusion. If the SIG infusion system 10a determines that the subject is having an adverse reaction based on the information acquired from the monitoring devices 32a, 32b, 32c, the SIG infusion system 10a can stop the infusion and notify the operator of the subject condition, thereby averting potential injury to the subject. Alternatively, the controller 14 may be programmed to make adjustments in the infusion protocol (e.g., decrease the rate of infusion or stop the infusion) in response to certain monitored changes in certain vital signs that may be a prodrome or early indication of an adverse reaction, thereby avoiding occurrence of a clinically significant or full blown adverse reaction.

Also, as shown in FIG. 2, in some embodiments a first telephony audio modem 28d may be connected to the SIG infusion system 10a and a second telephony modem 28e connected to a remote monitoring and control system 29 such as a personal computer. Modems 28d, 28e, connected together by wired or wireless telephony, may provide peer-to-peer connectivity means thus allowing a remote monitoring and control system 29 to interact with the SIG infusion system 10a directly. A remote monitoring and control system 29 may also communicate with the SIG infusion system 10a in a peer-to-peer connection via IEEE 802.11 or Bluetooth wireless interface. Lastly, the remote monitoring and control system 29 can be connected to a in-house network which includes IEEE 802.11 wireless access points devices through which the SIG infusion system, via IEEE 802.11 wireless interface, can communicate with the remote monitoring and control system 29, such as in a hospital environment.

Databases and Records

FIG. 3 illustrates an embodiment of a set of databases, folders, files, and/or records that are created, maintained, and accessed in the process of programming, selecting, and executing protocols for use by the SIG infusion system 10a. In this example, non-specific infusion protocols (comprising infusion protocol, infusion frequency, etc.), substance protocols (comprising substance name, manufacturer (if specified), diluent/solvent to be used, substance concentration in infusate, specific instructions of infusate preparation/reconstitution/dilution, etc.) and subject protocols (comprising specifications for subject's age, weight, date of birth, infusion protocol, etc.) are created by the operator using the SIG infusion system 10a or remotely on a personal computer 28a using an Infusion Configuration Program (ICP). Protocols created using an ICP may subsequently be transferred to the appropriate databases of the SIG infusion system 10a. A substance protocol may include information (e.g., substance name and concentration) relating to a specific therapeutic agent and optionally a link to a substance reference record 42 in a substance reference library 40 for the purpose of confirming that the substance protocol is within allowable parameters.

Infusion Protocol Database

In the example shown in FIG. 3, the infusion protocol database 26 provides storage for infusion protocols (e.g., non-specific infusion protocols and other information included in a particular infusion protocol). In this embodiment, infusion protocols may be categorized or organized in three therapy categories: IVIG, SQIG and CONT. The CONT therapy category is a continuous infusion mode wherein a continuous infusion is administered by a desired route of administration (e.g., intravenous, subcutaneous, epidural, etc.) Each therapy category can have any number of infusion protocols in it. In one embodiment, the therapy grouping is accomplished by use of file folders 34 maintained on a computer 28a with a flash disk drive or other suitable storage device. On the flash disk drive three file folders 34 are created, one for each therapy type. Non-specific infusion protocols are created and stored in file folders 34 according to therapy type.

Substance Protocol Database

The substance protocol database 22 stores substance protocols that are intended to be used when infusing particular substances as described generally hereabove. In this example, the substance database 23 is divided into three files or categories, namely IVIG, SQIG and CONT, in a manner similar to the infusion database. Each therapy category can have any number substance protocols for a verity of substance's (e.g., various different Immune Globulin preparations). In one embodiment, the therapy grouping is accomplished by use of file folders 38 maintained on a computer system with a flash disk drive or other suitable storage device. On the flash disk drive three file folders 38 are created, one for each therapy type. As substance protocols are created or downloaded, they are stored in the flash disk drive folder according to their therapy type.

Substance protocols stored in the substance protocol database 22 define infusion parameters and the substance to be infused. The substance to be infused may or may not exist as a substance reference record 42 in the substance reference library 40. If a substance reference record 42 for the particular substance is found in the substance reference library 40 (identified by substance name, concentration, and required administration route) then the parameters of the substance protocol are compared to corresponding program infusion limits found in the substance reference record 42. If a specific substance reference record 42 is not found in the substance reference library 40, the operator may then input the substance name, concentration, and required administration route and however, no comparison of the inputted parameters of the substance protocol to program infusion limits from a substance reference record 42 will be made nor will adverse reaction monitoring be performed. In this example, no subject data is included in the substance protocols stored in the substance protocol database 22.

It will be appreciated that adverse reaction feedback monitoring my be used even when no substance reference record 42 is in use. For example, the system may be programmed with absolute limits for monitored parameters (e.g., heart rate, body temperature, etc.) and when one or more of those absolute limits are exceeded, the controller 14 may undertake remedial measures such as a decrease of infusion rate or stop the infusion.

Subject Protocol Database

In this example, the subject protocol database 24 is used for storage of subject data and subject protocols for individual subjects to receive Immune Globulin infusions (either IVIG or SQIG) from this SIG system 10a. In many applications, such as in-hospital and home infusion applications, a single SIG infusion system 10a may be used to treat a number of different subjects and the subject protocol database 24 allows the SIG system 10a to store and recall information on each of those subjects. Subject-specific infusion protocols or other subject information may be organized and stored in separate folders 48 for each subject. The controller may be programmed to allow each subject folder 48 to contain only one set of subject information and no more than one of each type of therapeutic protocol (e.g., IVIG therapy protocol, SQIG therapy protocol, and CONT therapy protocol.) Alternatively, the controller may be programmed to allow each subject folder 48 to contain one set of subject information and multiple therapeutic protocols of each therapeutic types.

Substance Reference Library

The Substance Reference Library 40 provides storage for one or more substance reference records 42 or other substance information. In one embodiment, each substance reference record 42 may identify by substance name, substance concentration, and required administration route. A substance reference record 42 may also contain program infusion limits that the controller 14 will use to determine if the substance protocol to be executed is safely within the substance reference record limits. The substance reference record 42 may include various absolute infusion limits (e.g., absolute maximum infusion rate, absolute maximum volume to be infused, absolute maximum duration, and absolute minimum duration. In addition, the substance reference record 42 may include variable infusion limits dependent on subject's weight, age and/or gender. Therefore, when a subject's weight, age, and gender are known, a particular set of program infusion limits, more conservative than the absolute limits, may be retrieved from the substance reference record 42 for comparison to the infusion protocol parameters.

The substance reference record 42 also may contain a recommended total dose amount per a course of treatment based on a particular disease the subject may be suffering. When multiple protocols for the same substance are administered to the same subject, the SIG infusion system 10*a* may keep a running total of the amount of the particular substance the subject has received. If the running total of the amount of substance exceeds the specified total dose amount per course of treatment, then the SIG infusion system 10*a* may issue an alarm stopping the infusion and alerting the operator.

The substance reference record 42 may also include an adverse reaction symptom list 46 which contains a predetermined list of symptoms, the criteria for which the symptom is to be considered an adverse reaction, a classification of the adverse reaction, and additional text information to be presented to the operator via the user interface device 30 in the event that the adverse reaction is detected.

An optional pre-infusion checklist can be added to a substance reference record 42 and the controller 14 may be programmed to cause that pre-infusion checklist to be displayed to the operator before an infusion is begun. The pre-infusion checklist may contain textual instruction for the operator of the SIG infusion system 10*a* who is about to begin an infusion. Such instructions can remind the operator, for example, to make various vital signs checks of the subject prior to running the infusion and/or to be sure the subject had been pre-medicated.

FIG. 3 illustrates an embodiment that includes a substance reference library configurator program 44 that is operable on a personal computer 28*a* and useable to create and maintain the substance reference library 40. A substance reference library 40 may be created, and substance reference records 42 may be added, modified or deleted, using the substance reference library configurator program 44. In order to control access and integrity of the substance reference library, the substance reference library configurator program 44 cannot be operated on the SIG infusion system 10*a* itself.

The adverse reaction symptom selection list 46 is a list of physiologic symptoms that a subject may suffer during an infusion. In one embodiment, this list 46 is a list of various symptoms a subject may suffer during an infusion of IVIG. Such symptoms may include high or low blood pressure, high or low body temperature, low oxygen saturation level, high or low pulse rate, headache, shortness of breath, nausea, vomiting, lightheadedness and others. This list 46 may be merely representative and not exhaustive. The adverse reaction symptom selection list 46 is accessible by the substance reference library configurator program 44 for use by the operator in creation of a substance reference record 42.

The substance reference library 40 should be created and maintained by an authorized party of the institution responsible for the infusion. In as much as the substance reference library 40 may be critical to the safe infusion of IVIG and other substances, security of the substance reference library 40 may be important. In one embodiment, security of the substance reference library 40 may be accomplished by providing substance reference library configurator program 44 that properly interprets and modifies the contents of a substance reference library 40. Further, the substance reference library 40 itself may include one or several cyclic redundancy check (CRC) parameters which allows the substance reference library configurator program 44 to determine if the contents of the substance reference library 40 had been changed since the CRC parameters were last calculated and stored. In addition, pharmacists or administration personnel may be required to log into the substance reference library configurator program 44 by providing their username and password in order to operate the program. The authorized party may thereby create or modify substance reference records 42 by defining absolute infusion limits, one or more sets of program infusion limits based on weight, age, and gender of potential subjects, and maximum substance amount to be infused for a course of treatment based on the disease the subject may be suffering. The modified or newly created substance reference records 42 will then be applied to all substance infusion protocols 200 that reference the substance reference record 42. Sources of information needed to create or modify a substance reference record 42 are the substance manufacturers or as otherwise known in the medical infusion community.

In addition, the authorized party creating or modifying a substance reference record 42 may select appropriate symptoms from the adverse reaction symptom selection list 46 that relate to the infusion of the specific type of IVIG substance. For each selected adverse reaction symptom, criteria for classifying the adverse reaction as mild, moderate or severe is provided by the authorized party. For adverse reaction symptoms, mild, moderate, and severe, the authorized party may also define a message to be displayed to the operator on the occurrence of the mild, moderate or severe adverse reaction symptom. Sources for criteria constituting an adverse reaction are the substance manufacturer or as otherwise known in the medical infusion community.

After all substance reference records 42 have been entered into the substance reference library 40, the substance reference library 40 is saved to the personal computer 28*a* hard drive, or alternatively to a network server if the personal computer 28*a* is connected to a network. By use of the substance reference library configurator program 44, the authorized party may also perform maintenance functions on the substance reference library 40 such as renaming, erasing, copying, printing, or deleting substance reference records 42. A modified substance reference record 42 can be saved as a new substance reference record 42 or overwrite the original source substance reference record 42.

In order for a SIG infusion system 10*a* to use the substance reference library 40, the substance reference library 40 must be transferred to the SIG infusion system 10*a* by a communication means such as a wired or wireless interface device 28. Various wired interfaces are contemplated in this invention for communication between a personal computer 28*a* or network server and the SIG infusion system 10*a* such as EIA RS-232 serial interface, IEEE 802.3 Ethernet, and Universal System Bus (USB). Alternatively, wireless communication means such as IEEE 802.11 WiFi or Bluetooth technologies can be applied for the transfer of the substance reference library 40 to the SIG infusion system. Further, transfer of a substance reference library 40 from the computer 28a on which it has been prepared to the controller 14 of the SIG infusion system 10a, may be accomplished by use of data medium device such as a USB flash drive 28a'. In such instances, the substance reference library 40 will be copied to a folder on the USB Flash Drive 28a'. Then the USB Flash Drive 28a' is removed from the personal computer 28a or network system and inserted into a USB port of the SIG infusion system 10a and, after satisfying security access requirements, the substance reference library 40 is saved into the memory of the controller 14. Conversely, when it is desired to update or modify a substance reference library 40 (or any of the databases 22, 24, 26 stored in the controller 14 memory) such substance reference library 40 may be uploaded from the controller 14 to the USB Flash Drive 28a' and then transferred to the computer 28a where the desired updating or changes may be made.

Menus

Home Menu

Figure 7:
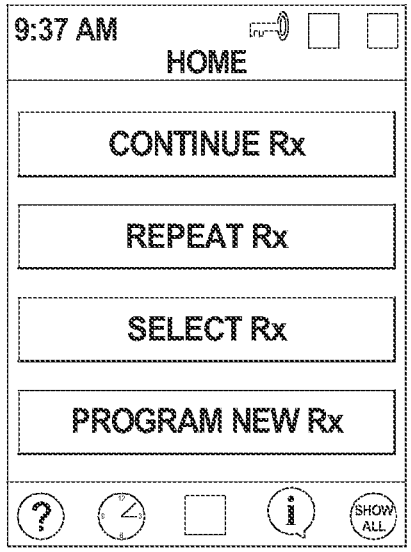
FIG. 7 shows an example of a home menu that may be displayed by an infusion system of the present invention.

In this example, all operator interaction with the SIG infusion system 10 begins at the "HOME" menu as shown in FIG. 7. When the SIG infusion system 10a is first turned on, the home menu is displayed on the LCD display. In addition, when no infusion is in progress, the SIG infusion system 10a menus will permit the operator to select to go to the home menu.

The HOME menu provides a varying list of selections based on the particular state of the SIG infusion system. The possible selections are: CONTINUE Rx, REPEAT Rx, SELECT Rx, and PROGRAM NEW Rx.

CONTINUE Rx

Figure 8:
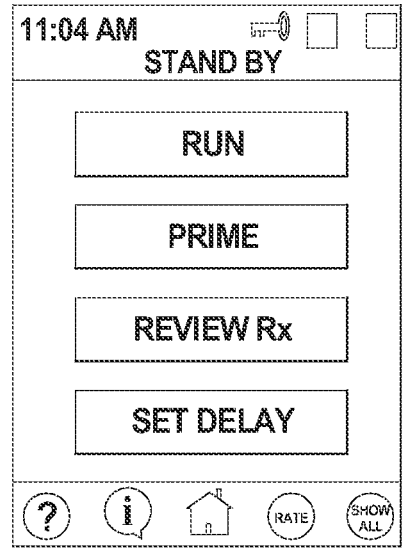
FIG. 8 shows an example of a standby menu that may be displayed by an infusion system of the present invention.

The CONTINUE Rx selection is available if an infusion was stopped before it was finished. If the operator chooses CONTINUE Rx, the operator is presented the standby menu, shown in FIG. 8.

REPEAT Rx

The REPEAT Rx selection is available if an infusion that had been in progress was either stopped or completed. If an infusion that was in progress was stopped before completion and an attempt to repeat the infusion protocol is made, then the controller 14 of the SIG infusion system 10a will alert the operator that proceeding will result in cancellation of the previously interrupted infusion. If no infusion had been in progress or if the operator acknowledges canceling of the infusion that was in progress, the Rx SUMMARY form shown in FIG. 9 will appear. If the operator accepts the Rx SUMMARY form, the SIG infusion system 10a will display the STANDBY menu, shown in FIG. 8, from which the operator can then run the infusion.

STANDBY Menu

The STANDBY menu is displayed when programming is complete, or accepting an Rx SUMMARY form, or when the CONTINUE Rx button is pressed on the HOME menu, and when clearing an Alarm. From the STANDBY menu, the operator can: a) run the infusion, b) prime the conduit, c) review/modify the infusion or d) set a delay start time for the infusion.

SELECT Rx

Figure 10:
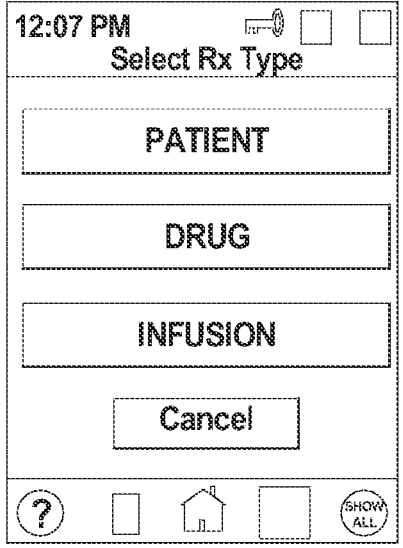
FIG. 10 shows an example of a select Rx menu that may be displayed by an infusion system of the present invention.

The SELECT Rx selection is available if there is at least one infusion protocol selectable from the database(s) 22 and/ or 24 and/or 26 stored in the memory of the controller 14. If the infusion in progress had been stopped and an attempt to select another infusion protocol is made, then the SIG infusion system alerts the operator that proceeding will cancel the Rx that had been stopped. If no infusion had been in progress or the operator acknowledges canceling of the Rx in progress, a SELECT Rx menu, shown in FIG. 10, is displayed allowing selection of a subject protocol from the subject protocol database, substance protocol form the substance protocol database, or an infusion protocol from the infusion protocol database.

PROGRAM NEW Rx

The PROGRAM NEW Rx is always an available selection on the HOME menu. If the infusion in progress had been stopped and an attempt to program new Rx is made, then the SIG infusion system alerts the operator that proceeding will cancel the Rx that had been stopped. If no Rx had been in progress or the operator acknowledges canceling of the Rx in progress, she will have the opportunity to create a new Rx as described later in this disclosure.

INITIATE Rx

In the event the SIG infusion system was programmed with an Rx or an Rx selected from an Rx database and the SIG infusion system was turned off, the subsequent turn on of the SIG infusion system will present the operator with the HOME menu; however, the INITIATE Rx selection will appear in place of the REPEAT Rx selection. When the operator selects the INITIATE Rx, the Rx SUMMARY form will be displayed. If the operator accepts the Rx SUMMARY form, the SIG infusion system 10a will display the STANDBY menu, shown in FIG. 8, from which the operator can then run the infusion.

Satisfy Security Requirements

When the operator selects REPEAT Rx, SELECT Rx, or INITIATE Rx, she may be required to enter an access code on the SIG infusion system via touch screen entry to satisfy security access. Alternatively, the operator might be required to identify herself to the SIG infusion system program by use of a barcode reader, attached to the SIG infusion system, which is used to read the operator's barcode information from her badge.

Rx SUMMARY

Figure 9:
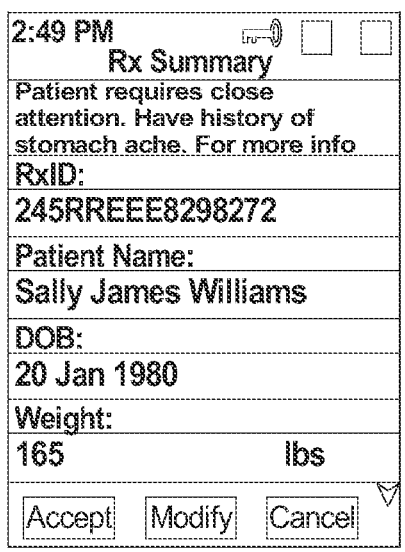
FIG. 9 shows an example of an Rx summary menu that may be displayed by an infusion system of the present invention.

Referring to FIG. 9, the Rx SUMMARY form provides a summary of the infusion parameters which the operator may accept, modify, or cancel. If the operator elects to modify the infusion parameters, the operator is then presented with the infusion programming screen (of the therapeutic type) and makes the desired modifications. After making modifications the operator accepts the modification and the infusion is checked against substance reference record 42 infusion limits if the Rx includes a reference to an existing substance reference record 42. The operator can then save the modified infusion as a new infusion protocol, if applicable, or overwrite the original infusion protocol.

Creating a New Infusion Protocol

Satisfy Security Requirements

Figure 4:
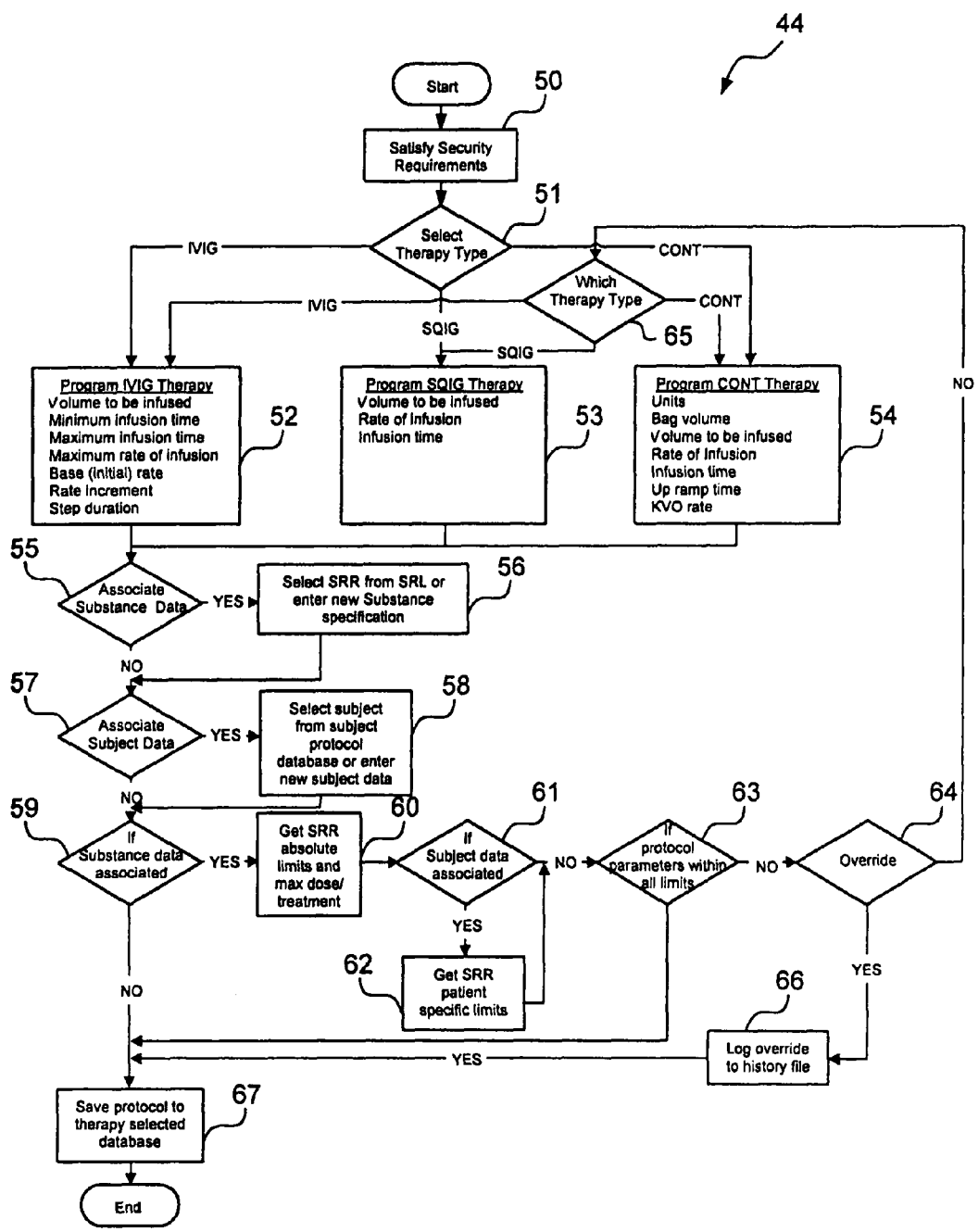
FIG. 4 is a flow diagram of a method for creating and storing a new infusion protocol to be used by an infusion system of the present invention.

FIG. 4 illustrates a method of creating an infusion protocol. The SIG infusion system 10a allows programming an infusion protocol after the operator has satisfied the security requirements 50 of the SIG infusion system 10. In one embodiment, the operator may be required to enter an access code on the SIG infusion system 10 via touch screen. Alternatively, the operator might be required to identify herself to the SIG infusion system 10a by use of a barcode reader 28c to read the operator's barcode information from a badge, identification card or the like.

After the operator has satisfied the SIG infusion system's security requirements, the SIG infusion system 10a program displays a select therapy menu 51 from which the operator selects the therapy type: IVIG, SQIG, or CONT. The operator then makes a selection of one of the therapy types and proceeds to program the infusion parameters.

IVIG Infusion Parameters

In the case of IVIG therapy type, the operator inputs IVIG infusion parameters 52 for: volume to be infused, minimum infusion time, maximum infusion time, maximum rate of infusion, base (initial) rate of infusion, rate increment, and step duration.

Figure 11:
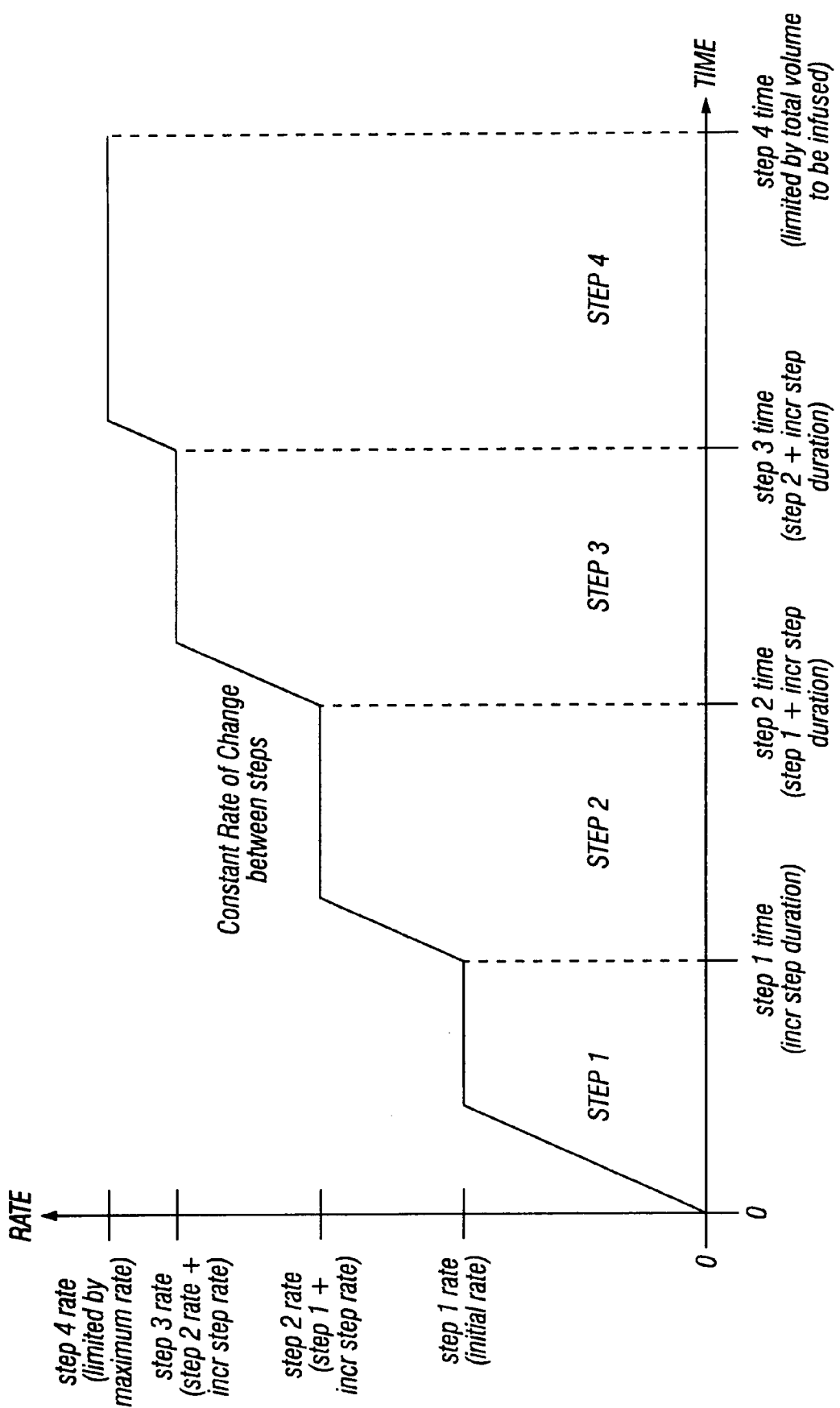
FIG. 11 is a graph of Infusion Rate v. Time, showing an example of an IVIG infusion profile that may be delivered using an infusion system of the present invention.

In the present invention, the infusion profile is calculated from the infusion parameters prior to starting the infusion. One example of such IVIG infusion profile is shown graphically in FIG. 11. The infusion profile may consist of one or several steps wherein each step includes up to two segments. The first segment provides an approximate constant change of rate or ramping segment (e.g., 12 milliliters/hour/second) from the terminal rate of the previous step (or zero in the case of being the first step to be executed) to the terminal rate of the current step. This is represented on FIG. 11 by the initial up-sloped line at the beginning of each of Steps 1, 2, 3 and 4. Once the terminal rate has been achieved in any step, that step continues at the terminal rate until the volume to be infused for that step has been delivered, or until the step duration has elapsed. This is represented in FIG. 11 by the flat line that follows the initial up-sloped line in each of Steps 1, 2, 3 and 4. Where the change of rate is sufficiently high (e.g., 12 milliliters/hour/second), the minimum step duration sufficiently long (e.g., 300 seconds) and the maximum rate of infusion is sufficiently limited (e.g., 1000 milliliters/hour), each step will reach its terminal rate before the step has terminated (except potentially the last step during which it is possible that all the volume to be infused for the entire infusion has been delivered before the terminal rate of the last step has been reached.) For example, where a single step is to start from an initial rate of 0 milliliters/hour and reach a maximum rate of 1000 milliliters/hour and the constant change of rate is approximately 12 milliliters/hour/sec (thereby maximizing the duration of ramping), the step will finish its first or ramping segment in 83.3 seconds which is much less than the minimum step duration of 600 seconds; therefore, a terminal rate segment must follow the ramping segment.

The series of infusion profiles steps are computed by calculating the first step and then subsequent steps. The ramp segment of the first step starts at a zero milliliters per hour rate and increases, at an almost constant rate, until the rate reaches the base (initial) rate. The calculated volume delivered by the first step is calculated as the sum of the volume during the ramping segment and the terminal rate segment. The remaining volume is then calculated as the total volume to be infused minus the volume of the first step. The number of possible remaining steps can next be calculated by dividing the difference of the maximum rate of infusion and the base (initial) rate of infusion by the rate increment, rounding the quotient up, and adding one to the quotient. The computations for each of the subsequent infusion steps is generally calculated by starting the ramp segment at the terminal rate achieved by the prior step and increasing the rate, by a constant change of rate, until one full rate increment has been added to the terminal rate of the prior step; thereafter following with a terminal rate segment maintaining the rate achieved at the end of the ramp segment. The calculated volume delivered for each step is subtracted from the remaining volume and if the remaining volume is reduced to zero or less, the step being calculate is considered the last step having a reduced volume and execution time sufficient only to deliver the last of the remaining volume. If at any time the calculated rate of a step would exceed the maximum rate, the rate of that step is limited to the maximum rate. In addition, as the steps are calculate, their execution time is summed up and if their total execution time becomes equal to, or greater than, the maximum infusion time, that step under calculation will be the last step and will terminate so that the infusion time will not exceed the maximum infusion time. In the case where the rate of the last step (e.g., Step 4 in FIG. 11) has been limited by the maximum rate of infusion, the calculation for that step's duration will be extend until all of the volume to be infused has been delivered or until the maximum infusion time has been reached.

SQIG Infusion Parameters

In the case of SQIG therapy type, the operator inputs SQIG infusion parameters 53 for (or their value is calculated): volume to be infused, rate of infusion, and time of infusion. Time of infusion is calculated when volume to be infused and rate of infusion are entered.

CONT Infusion Parameters

In the case of a continuous infusion therapy, the operator inputs continuous infusion parameters 54 for (or their value is calculated): the units of measurement to be used (e.g., milliliters (ml), milligrams (mg), or micrograms (mcg)), the concentration of substance in the infusate (if weight units such as milligrams or micrograms had been selected), total volume of infusate (e.g., "bag volume"), the volume or amount of infusate to be infused, up ramp time, infusion rate (after up ramp completed), total infusion time, and the keep vein open (KVO) infusion rate.

TPN Infusion Parameters

In the case of a total parental nutrition (TPN) infusion therapy, the operator inputs parameters for (or their value is calculated): the volume to be infused, up ramp time, infusion rate (after up ramp completed), down ramp time, total infusion time, and the keep vein open (KVO) infusion rate. Total infusion time is calculated when volume to be infused, rate of infusion, up ramp time, and down ramp time are entered.

Selecting a Substance Reference Record 42 to be Used with the Infusion Protocol

The operator may choose to associate 55 the infusion protocol with an existing substance reference record 42, create a new substance specification 56 by defining substance name, concentration, and administration route, or not associate the Rx with any substance information. If the operator creates a new substance specification, the new specification will not be added to the substance reference library 40 and will be used as textual information only by this infusion.

Associating Subject Data with the Non-Specific Infusion Protocol

The operator may choose to associate 57 previously defined subject information from the subject protocol database 24 or to input new subject information to be associated with a new subject. Subject information may include subject's name, date of birth, weight, and gender.

Check Programmed Infusion Parameters Against Limits

After programming all infusion parameters and choosing whether to associate the Rx with an existing substance reference record 42 and subject data, the SIG infusion system will check the programmed infusion parameters against predefined absolute limits 60 found in the substance reference record 42 and, if subject information is provided, further check against more conservative limits specific to subject information 62. For example where the weight of the subject is known and substance reference record contains limits that are weight specific, the subject's weight may be used to determine if a more specific limit should be applied to the infusion parameters. Age can also be used as a subject specific characteristic that can activate more conservative limits if the drug reference record contains such limit definitions.

The SIG infusion system may also check the expected volume to be delivered during the infusion will not violate the maximum dose amount per course of treatment. If the addition of the expected volume to be delivered will exceed maximum dose amount per course of treatment 63, the operator, after satisfying access code requirements, is given the opportunity to override 64 the limit check violation. If the operator overrides the limit check violation, the override event is logged to the history file 66 and the infusion is save to a database 67. If the operator does not override the limit check violation 65, the programmed infusion parameter in violation must be modified to be within limits or the controller will prevent the infusion from being started.

If the infusion is not associated with a substance reference record 42, then no checking for substance reference record 42 related limits is performed and the infusion protocol is saved 67 into the appropriate database 22, 24, 26.

Save Created Rx to a Database

After programming all infusion parameters and checking the parameters against limits found in the associated substance reference record 42, the infusion is saved to the appropriate database 22, 24, 26. In one embodiment, if the infusion protocol does not include any substance specification or subject specification, it is saved 67 to the infusion protocol database 26 under the therapy specific folder 34 (IVIG, SQIG, or CONT). If the infusion protocol does not contain subject information but does contain a substance specification, whether or not that substance specification is found in the substance reference library 40, the infusion is saved 67 to the substance protocol database 22 under the therapy specific folder 38 (IVIG, SQIG, or CONT). If the infusion protocol contains subject information then that infusion protocol, including the subject information, is saved 67 to the subject protocol database 24 in that subject's folder 48.

Infusion Configuration Personal Computer Program

The Infusion Configuration Program (ICP) is a program, operable on a personal computer 28a that simulates programming of infusion protocols directly on the SIG infusion system 10a. The ICP creates subject protocols, substance protocols or non-specific infusion protocols which can be transferred to the appropriate database 22, 24, 26 of the SIG infusion system 10a via any of the above mentioned connectivity mediums 28a-28e.

Selecting an Existing Infusion Protocol from a Database

Figure 5:
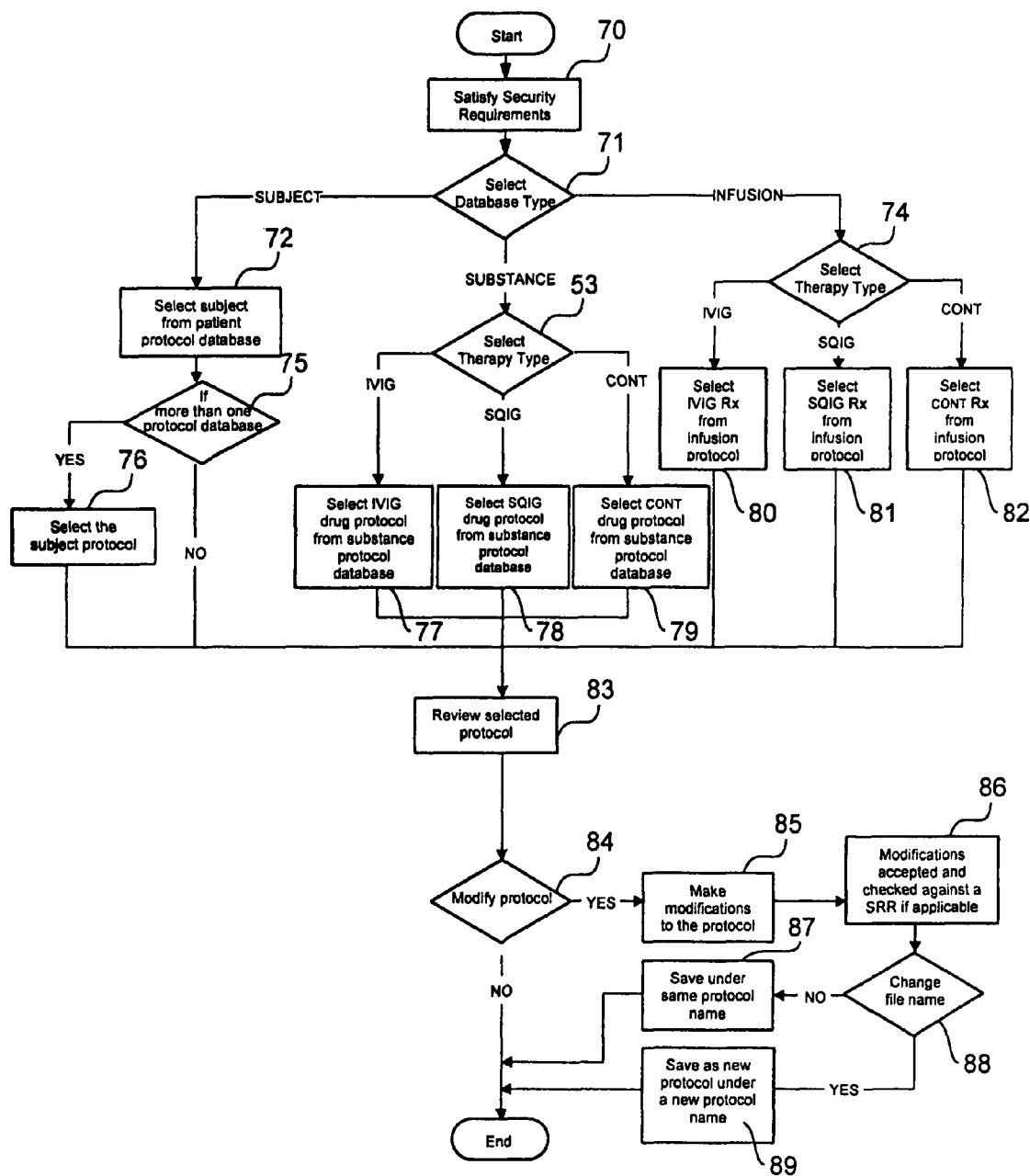
FIG. 5 is a flow diagram showing alternate methods that may be used for selecting and optionally modifying an infusion protocol to be used by an infusion system of the present invention.

FIG. 5 illustrates the selection of an infusion protocol from the subject, substance, and infusion databases 22, 24, 26.

Selecting a Subject-Specific Infusion Protocol

In order to select an existing subject infusion protocol from a subject protocol database 24 for infusion, the operator must satisfy the SIG infusion system's security requirements 70. In one embodiment, the operator may need to enter an access code on the SIG infusion system via touch screen entry to satisfy security access. Alternatively, the operator might be required to identify herself to the SIG infusion system program by use of a barcode reader 28c to read the operator's barcode information from a badge, identification card or the like.

In one embodiment, the operator is presented with a selection list 71 whereby the operator may select the substance protocol database 22, subject protocol database 24 or infusion protocol database 26. If the operator selects the subject database, she is presented with a list of subjects (e.g., subjects or clinical study participants) from which the operator must select 72. After the operator selects a particular subject 72, if there is more than one subject-specific infusion protocol available for that subject 75, a list of available infusion protocols will be displayed for selection 76. Following the selection of the desired infusion protocol for that subject, the operator is presented with a summary of the infusion protocol 83 which the operator may elect to accept, modify, or cancel.

If the operator chooses to modify the selected infusion protocol, she is presented with the infusion programming screen and may make desired modifications 85. After making modifications, the operator accepts the modification and the subject-specific infusion protocol is checked against infusion limits for that substance that may be contained in the substance reference library 40. If there is a substance reference record 42 for that substance and the infusion parameters do not violate the limits set in that substance reference record 42, the operator can then save the modified subject-specific infusion protocol by overwriting the original 87. Alternatively, the operator may elect to save the modified subject-specific infusion protocol saved under a new subject name without modifying the original source protocol in the database.

Selecting a Substance Infusion Protocol

In order to select an existing substance infusion protocol from the substance protocol database 22 for infusion, the operator must satisfy the SIG infusion system's security requirements 70. In one embodiment, in order to select an existing substance-specific infusion protocol, the operator may need to enter an access code on the SIG infusion system via touch screen entry to satisfy security access. Alternatively, the operator might be required to identify herself to the SIG infusion system program by use of a barcode reader 28c which is used to read the operator's barcode from the operators badge, identification card or the like.

In one embodiment the operator is presented with a selection list containing selectable databases 71, such as the substance protocol database, subject protocol database and therapy-type protocol database. If the operator selects the substance protocol database, she is presented with a list of therapeutic types 73: IVIG, SQIG, or CONT. If the operator selects IVIG, she is presented a list of IVIG substance protocol records from the substance protocol database 77. If the operator selects SQIG, she is presented a list of SQIG substance protocols from the substance protocol database 78. If the operator selects CONT, she is presented a list of CONT substance protocols from the substance protocol database 78. After selecting a substance-specific infusion protocol, the operator is presented with a summary of the substance-specific infusion protocol parameters 83 to which the operator may accept, modify, or cancel.

If the operator chooses to modify the selected protocol 84, she is presented with the infusion programming screen and may make desired modifications 85. After making modifications, the operator accepts the modification and, if the substance-specific infusion protocol includes a reference to an existing substance reference record 42, the infusion is checked against substance reference record 42 infusion limits 86. The operator can then save the modified infusion as a new substance protocol 89 or overwrite the original 87.

If the operator accepts the originally selected substance protocol or accepts and saves a modified substance protocol, the substance protocol is loaded into the SIG infusion system for infusion.

Selecting an Infusion Protocol Based on Therapy Type

In some embodiments, the system includes a therapy-type infusion protocol database 26. In order to select an existing therapy-type infusion protocol from the therapy-type infusion protocol database 26, the operator must satisfy the SIG infusion system's security requirements 70. In one embodiment, in order to select an existing protocol from the therapy-type infusion protocol database, the operator may need to enter an access code on the SIG infusion system via touch screen entry to satisfy security access. Alternatively, the operator might be required to identify herself to the SIG infusion system program by using a barcode reader 28c to read a barcode on the operator's badge, identification card or the like.

After gaining access to the system, the operator is presented with a selection list of some or all of the available databases. For example, the operator may view a screen that allows the operator to select either the substance protocol database 22, subject protocol database 24 or therapy-type protocol database. If the operator selects the therapy-type protocol database 26, she is then presented with a list of therapeutic types 74, such as: IVIG, SQIG, or CONT. If the operator selects IVIG, she is then presented a list of one or more IVIG infusion protocol(s) which are suitable for, or have been historically used for, IVIG therapy but which are not specific to any particular substance or any particular subject. If the operator selects SQIG, she is then presented a list of one or more SQIG infusion protocol(s) which are suitable for, or have been historically used for, SQIG therapy but which are not specific to any particular substance or any particular subject. If the operator selects CONT, she is presented a list of one or more CONT infusion protocols which are suitable for, or have been historically used for, CONT therapy but which are not specific to any particular substance or any particular subject. After selecting a therapy-type infusion protocol, the controller may then present the operator with a summary of the infusion parameters 83, some or all of which may then be accepted, modified or cancelled by the operator.

If the operator chooses to modify the selected infusion protocol 84, she is presented with the infusion programming touch screen presentation that may be used by the operator to make the desired modifications 85. After making modifications, the operator can then save the modified infusion protocol as a new therapy-type infusion protocol 89 or overwrite the original therapy-type infusion protocol that had been modified.

If the operator accepts the originally selected therapy-type infusion protocol, or if the operator accepts and saves a modified therapy-type infusion protocol, the controller will then load the selected protocol into the SIG infusion system 10a for infusion.

Standby Menu

After a particular infusion protocol has been accepted by the operator for infusion or if the operator stops an infusion that is in progress, the operator is presented with a "standby" menu (FIG. 8) allowing her to "run", "prime", and "review/modify Rx". In the event that the operator stopped an infusion in progress, a "status" selection is provided to allow review of the progress of the now stopped infusion.

Run

Selecting run displays a confirmation run menu asking if it is proper to start the infusion. Selecting yes to the confirmation menu will cause the infusion to begin running. The SIG infusion system then starts pumping and administers the substance according to the loaded Rx infusion parameters.

Prime

The prime feature allows the operator to prime the administration set with fluid, replacing any air that may be in the administration set. Selecting prime displays a prime advisory menu instructing the operator to disconnect the SIG infusion system from the subject. After the operator responds to the prime advisory menu, the prime screen is displayed instructing the operator to press and hold the prime button to prime the administration set. Pressing and holding the prime button will cause up to three milliliters, for example, of fluid to prime the administration set. If the prime button is released or three milliliters of priming has occurred, the priming will stop. Releasing and then pressing the prime button again will cause the prime to resume and allow up to another three milliliters to be pumped.

Review/Modify Rx

The review/modify Rx feature allows the operator to review the infusion parameters for the Rx that is loaded. In addition, if subject information and/or substance data is associated with the loaded Rx, then that data may also be reviewed. If the operator desires, the Rx under review may be modified if the operator can satisfy the SIG infusion system security requirements.

IVIG Infusion Profile

When infusing an IVIG therapy, the IVIG rate profile starts at the base rate and then increases by the rate increment when the step duration has elapsed. This process of increasing the rate by the rate increment continues at the elapse of the step duration until the maximum rate is achieved or the volume to be infused has been delivered. If in the last step a full rate increment increase would exceed the maximum rate, the final rate is the maximum rate only. The transition from one rate to another is attained by a controlled ramp to ease the physiological effects of the sudden increase of substance delivery to the subject. Once an infusion reaches the maximum rate, the infusion continues at the maximum rate until the volume to be infused has been delivered.

SQIG Infusion Profile

When infusing a SQIG therapy, the SQIG rate of infusion ramps up to the programmed rate of infusion in a controlled manner. Once an infusion reaches the programmed rate, the infusion continues at that rate until the volume to be infused has been delivered.

CONT Infusion Profile

When infusing a CONT therapy, the CONT rate of infusion ramps up to the programmed rate of infusion according to a programmed up ramp time parameter. Once the up ramp time has elapsed and the rate of infusion reaches the programmed rate, the infusion continues at that rate until the remaining volume to be infused has been delivered. After finishing the delivery of all the volume to be infused, the SIG infusion system will run at the programmed KVO rate.

Realtime Display of Infusion Progress

When the infusion begins running, the infusion status screen is displayed showing: volume infused, remaining volume to be infused, current rate, target rate, infusion time, and remaining time. For IVIG therapy, current step is included on the infusion status screen.

Interaction by Operator with an Infusing Rx

While an infusion is running, the operator may interact with the infusion by stopping (pausing) or titrating the infusion.

Stopping an Infusion

Anytime that an infusion is running, the operator my stop the infusion by pressing a stop button. So doing will cause the infusion to stop and display the standby menu, providing selections of run, prime, review/modify Rx and status.

Titrating

While the SIG infusion system is running an infusion, the operator can choose to titrate or change the infusion rate by pressing a button on the infusion status menu. Changing the infusion rate may require the operator to enter an access code on the SIG infusion system via touch screen entry to satisfy security access. Alternatively, the operator might be required to identify herself to the SIG infusion system program by use of a barcode reader, attached to the SIG infusion system, which is used to read the operator's barcode information from her badge.

If the therapy type is IVIG and therefore has a stepping profile, a screen is displayed giving the operator the choice of keeping the current stepping profile or finishing the remainder of the infusion at the new infusion rate. Retaining the stepping profile may cause the number of steps in the remainder of the infusion to be recalculated.

Adverse Reaction Monitoring

Adverse reaction monitoring (ARM) monitors the subject's vital signs and subject's symptom responses to help the operator determine if the subject is having an adverse reaction to the infusion. In order to use ARM, the SIG infusion system must be loaded with a substance protocol for which a substance reference record 42 exists in the substance reference library 40. Prior to using ARM for vital signs, subject's vital signs data must be taken to establish a baseline reference for subsequent reading of vital signs.

Vital Signs

Vital signs monitoring is the periodic acquisition of physiological vital signs data from a subject. Vital signs to be monitored and the frequency of monitoring are determined by the institution responsible for the infusion and found in the substance reference record 42. Vital signs monitored include blood pressure, temperature, pulse rate, oxygen saturation level, etc. Vital signs data may be acquired automatically by the SIG infusion system if it is connected to automated vital signs monitoring equipment and the subject is connected to the automated vital signs monitors. Where no automated vital signs monitoring equipment is available, vital sign data may manually be entered into the SIG infusion system. The scheduling of vital sign acquisition and detecting of adverse reaction based on vital signs data is set by parameters in the substance reference record 42 and the programmed protocol.

Subject Symptom

Subject symptom monitoring is the periodic acquisition of subject symptoms. Subject symptoms to be monitored and the frequency of monitoring are determined by the institution responsible for the infusion and found in the substance reference record 42. Typical subject symptoms monitored include headache, light-headedness, chills, shortness of breath, nausea or vomiting, etc. When prompted by the SIG infusion system, the operator will determine the subject's condition relative to the symptom being asked by the SIG infusion system. The operator must manually enter the subject symptom responses to the SIG infusion system; there is no automatic entry of subject symptoms. The scheduling of acquisition of subject symptoms and detecting of adverse reaction based on subject symptom data is set by parameters in the substance reference record 42 and programmed protocol.

Detection and Handling of Adverse Reactions

Figure 6:
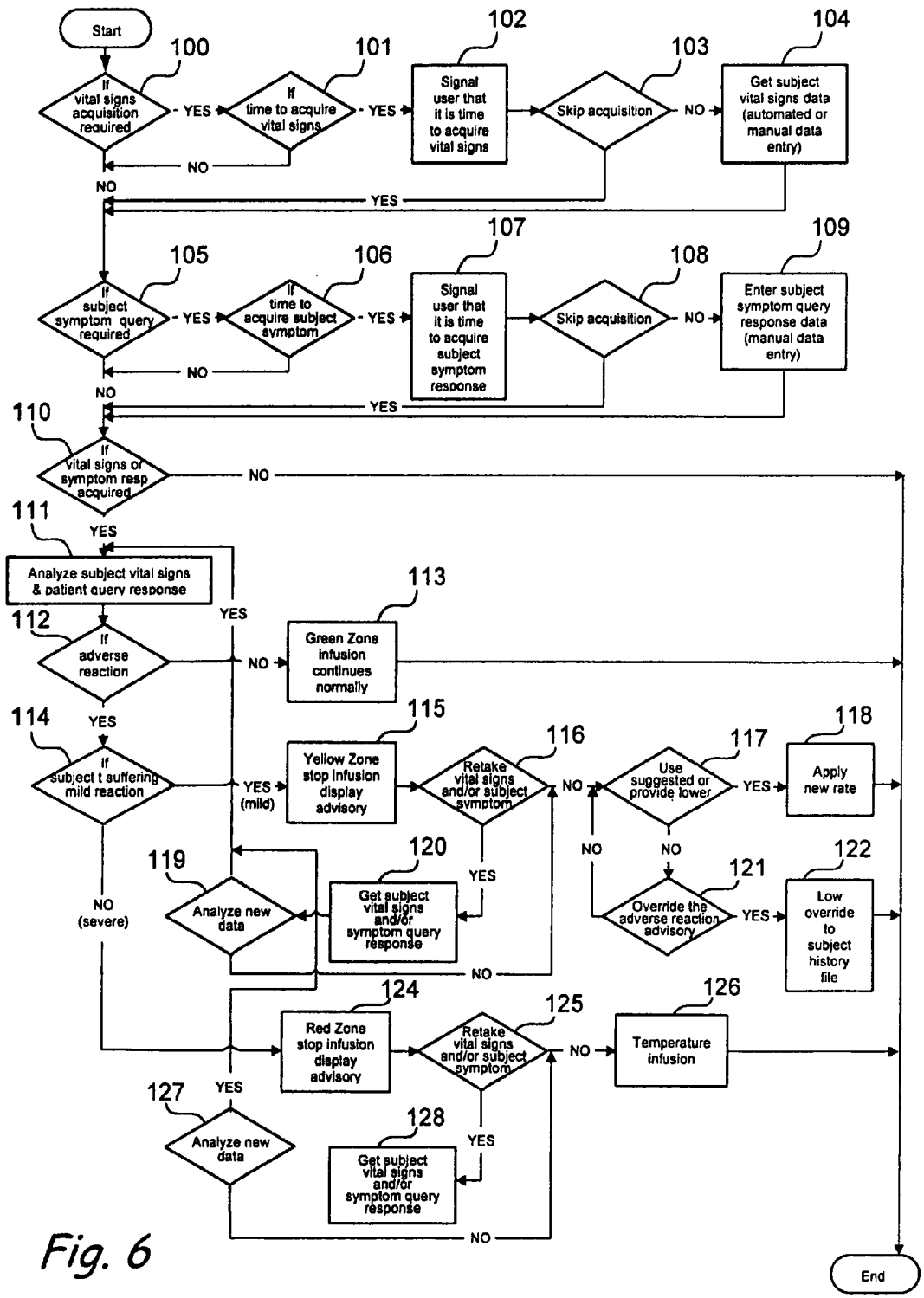
FIG. 6 is a flow diagram showing an embodiment of the present invention wherein an infusion system is used to administer an infusion to a patient while monitoring the patient's response to such infusion.

Referring to FIG. 6, if the substance reference record 42 has been setup to require the acquisition of vital signs data 100 and, according to vital signs monitoring schedule, the acquisition of vital signs is due within two minutes, then the operator is notified of the approaching scheduled vital signs acquisition by an audible beep and message on the display. When it is time to acquire vital signs 101, a menu is displayed 102 to the operator so indicating. This menu 102 includes a selection that allows the operator to skip the acquisition of vital signs. If the operator chooses to skip the acquisition of vital signs 103, she must enter an access code and an entry is made to the history file indicating the acquisition of vital signs was skipped. If the system includes automated vital signs monitoring equipment connected to the SIG infusion system, the SIG infusion system will automatically initiate the acquisition of vital signs data 104; otherwise, the operator is prompted to enter the vital signs data 104 on the SIG infusion system manually. If the substance reference record 42 has not been setup to require the acquisition of vital data then no prompt or attempt to acquire vital signs is made. If the substance reference record 42 has been setup to require vital sign data be acquire but, according to vital signs monitoring schedule, it is not time to acquire vital signs, no prompt or attempt to acquire vital signs is made.

If the substance reference record 42 has been setup to require the acquisition of subject symptom responses 105 and if according to the subject symptom query monitoring schedule the acquisition of subject symptom responses is due in two minutes, the operator is notified of the approaching scheduled subject symptom response acquisition by an audible beep and message on the display. When it is time to acquire subject symptom responses 106, a menu is displayed 107 to the operator so indicating. This menu 107 includes a selection that allows the operator to skip the acquisition of subject symptom responses. If the operator chooses to skip the acquisition of subject symptom responses 108, she must enter an access code and an entry is made to the history file indicating the acquisition of subject symptom responses was skipped. If the operator does not skip the acquisition of subject symptom responses, the operator then manually enters 109 the subject symptom responses as prompted by the menu displayed. If the substance reference record 42 has not been setup to require the acquisition of subject symptom responses, then no prompt to acquire subject symptom responses is made. If the substance reference record 42 has been setup to require the acquisition of subject symptom responses but, according to subject symptom monitoring schedule, it is not time to acquire subject symptom responses, no prompt to acquire subject symptom responses is made.

If vital signs data and/or subject symptom responses had been acquired 110, they are analyzed according to the limits and parameters setup in the substance reference record 42 associated with the infusion 111. If no adverse reaction is thereby detected 112, the subject is considered sufficiently tolerant of the infusion and a designation of "green zone" is used to describe the subject's condition. The SIG infusion system will continue to run the infusion while the subject is in a green zone condition.

If the subject is suffering a mild adverse reaction 114, as determined by the analysis described above, the infusion stops and the subject's condition is classified as a "yellow zone" condition 115. For a yellow zone condition, the operator is given the opportunity by the SIG infusion system to retake or enter the vital sign(s) and/or subject symptom(s) 116 related to the reason the mild adverse reaction was detected. If the operator retakes and enters the vital sign(s) and/or subject symptoms(s) 120 the operator is given the opportunity to have the new data analyzed 119 according to the limits and parameters setup in the substance reference record 42. If the operator chooses to analyze the new data, processing for detection of adverse reactions starts anew. If the operator chooses not to analyze the new data or if she chooses not to retake vital sign(s) and/or subject symptom(s), the SIG infusion system will suggest a lower infusion rate and allow the operator to accept the lower suggested rate or enter an even lower rate to be used when the infusion is resumed 117. If the operator chooses to use the suggested lower rate or a lower rate she had entered, then the new lower rate is applied 118 and used when the infusion is resumed. If the operator chooses not to use the suggested lower rate or enter an even lower rate, then the operator is given the opportunity to override the mild adverse reaction advisory 121. If the operator chooses to override the mild adverse reaction advisory, she is required to provide an access code and her action is recorded to a history file 122. If the operator chooses not to override the adverse reaction advisory, she is again given the opportunity to accept the SIG infusion system suggested lower infusion rate or enter an even lower infusion rate.

If the subject is suffering a severe adverse reaction 114, as determined by the analysis described above, the infusion stops and the subject's condition is classified as a "red zone" condition 124. For a red zone condition, the operator is given the opportunity by the SIG infusion system to retake and enter the vital sign(s) and/or subject symptom(s) 125 related to the reason the severe adverse reaction was detected. If the operator retakes and enters the vital sign(s) and/or subject symptom(s) 128 the operator is given the opportunity to have the new data analyzed 127 according to the limits and parameters setup in the substance reference record 42. If the operator chooses to analyze the new data 127, processing for detection of adverse reactions starts anew. If the operator chooses not to analyze the new data or if she chooses not to retake vital sign(s) and/or subject symptom(s), the infusion is terminated 126 and cannot be resumed.

History Database

A history files or log is used in the SIG infusion system to record infusion activities, malfunctions, alarms, alerts, advisories and events that may occur while the SIG infusion system is turned on. The history file records the activities normally associated with setting up and operating the SIG infusion system. Information such the Infusion protocol parameters for an infusion, modifications to an Infusion protocol, occurrences of alerts, alarms and malfunctions, the operator selecting to override of limits or suggestions made by the SIG infusion system, and all activities which required the operator to provide an access code to perform. By using an access code, the history file can be reviewed on the SIG infusion system, copied to a personal computer, and printed. In addition, the history file can be cleared by using an authorizing access code. However, though the history file appears cleared to normal operators, its contents prior to clearing are maintained by the SIG infusion system and may be reviewed and retrieved by factory personnel via factory access code.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example un-novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. An infusion device comprising a pump that delivers an infusate to a human or animal subject and a controller programmed to: (i) control a delivery of the infusate in accordance with an infusion profile stored in a storage medium and (ii) monitor whether the patient is suffering an adverse reaction, the adverse reaction stored in a substance reference library in the storage medium in association with the infusate, said infusion profile comprising:
   a. a total volume or total amount of infusate to be infused;
   b. at least three infusion steps, each infusion step having an infusion rate and a duration, wherein the total volume or amount of infusate is infused over the at least three infusion steps; and
   c. a constant rate of change between the infusion rate between each of the infusion steps, wherein the constant rate of change has a slope between zero and ninety degrees relative to a horizontal time axis.

2. A device according to claim 1 wherein the constant rate of change is selected by an operator.

3. A device according to claim 1 wherein the infusion profile includes the infusion rates and durations of a plurality of subsequent infusion steps and constant rates of change in infusion rate between each of said subsequent infusion steps.

4. A device according to claim 1, wherein the controller is programmed to monitor whether the subject is suffering an adverse reaction by monitoring a plurality of vital sign monitors.

5. A device according to claim 1, wherein the controller is programmed to monitor whether the subject is suffering an adverse reaction by presenting queries to the subject and monitoring responses from the subject.

6. A device according to claim 5, further comprising a reference library of responses with a list of responses that suggest no adverse reaction and a list of responses that suggest an adverse reaction.

7. A device according to claim 5, wherein the controller is programmed to halt or reduce the infusion rate if the responses from the subject are determined to be unacceptable.

8. A device according to claim 5, wherein the controller is programmed to provide an alarm or notice to a user if the responses from the subject are determined to be unacceptable.

9. A device according to claim 5, wherein the controller is programmed to take a remedial action if the responses from the subject are determined to be unacceptable.

10. A device according to claim 1, further comprising a plurality of vital sign monitors operably connected to the controller.

11. An infusion device for administering a substance to a human or non-human subject, said infusion device comprising:
    a pump;
    a controller in communication with the pump and configured to (i) issue control signals to the pump, (ii) control a delivery of the substance in accordance with an infusion profile and (iii) continuously monitor a plurality of vital sign monitors to determine whether the patient is suffering an adverse reaction to the substance, wherein the infusion profile includes: (a) a total volume of infusate to be infused; (b) a plurality of infusion steps, each infusion step having an infusion rate and a duration, wherein the total volume of infusate is infused over the plurality of infusion steps; and (c) a constant rate of change between the infusion rate between each of the infusion steps, wherein the constant rate of change has a slope between zero and ninety degrees relative to a horizontal time axis;

a conduit for delivering the substance to the subject's body; and a storage medium that contains (i) a controller-accessible substance reference library database storing at least one adverse reaction associated with the substance, the controller configured to access the controller-accessible substance reference library to determine whether the patient is suffering an adverse reaction to the substance and (ii) at least one controller-accessible database selected from the group of databases consisting of: (a) a substance protocol database, (b) a subject protocol database, (c) a therapy-type protocol database, (d) a system configuration database, (e) a history database and (f) combinations thereof.

12. A device according to claim 11, wherein the controller is configured to stop or modify the infusion profile if the subject is suffering an adverse reaction.

13. A device according to claim 11, wherein the controller is configured to present a series of queries to the subject to determine whether the subject is suffering an adverse reaction.

14. A device according to claim 11, wherein the storage medium further comprises a list of adverse reaction symptoms.

15. A device according to claim 14, further comprising a computer and an input apparatus configured to present queries to the subject, monitor a subject's response to the queries, and store information regarding the subject's responses to the queries.

* * * * *